US009289348B2

(12) United States Patent
Kanbar et al.

(10) Patent No.: US 9,289,348 B2
(45) Date of Patent: Mar. 22, 2016

(54) PERSONAL MASSAGER

(71) Applicants: Maurice S. Kanbar, San Francisco, CA (US); Albert Kolvites, San Mateo, CA (US)

(72) Inventors: Maurice S. Kanbar, San Francisco, CA (US); Albert Kolvites, San Mateo, CA (US)

(73) Assignee: Maurice S. Kanbar Revocable Trust, San Francisco, CA (US)

(*) Notice: Subject to any disclaimer, the term of this patent is extended or adjusted under 35 U.S.C. 154(b) by 0 days.

(21) Appl. No.: 14/087,841

(22) Filed: Nov. 22, 2013

(65) Prior Publication Data

US 2015/0148592 A1 May 28, 2015

(51) Int. Cl.
*A61F 5/00* (2006.01)
*A61H 19/00* (2006.01)

(52) U.S. Cl.
CPC ........ *A61H 19/34* (2013.01); *A61H 2201/0153* (2013.01); *A61H 2201/1215* (2013.01); *A61H 2201/1253* (2013.01); *A61H 2201/1481* (2013.01)

(58) Field of Classification Search
CPC ....... A61H 19/00; A61H 19/30; A61H 19/34; A61H 19/40
USPC .................................. 600/38–41; 601/46, 84
See application file for complete search history.

(56) References Cited

U.S. PATENT DOCUMENTS

| | | | |
|---|---|---|---|
| 2,263,219 A | 11/1941 | Lybarger | |
| 3,504,665 A | 4/1970 | Bakunin et al. | |
| 3,978,851 A | 9/1976 | Sobel | |
| 5,460,597 A | 10/1995 | Hopper | |
| 5,470,303 A | 11/1995 | Leonard et al. | |
| 6,632,185 B2 | 10/2003 | Chen | |
| 2007/0015435 A1 | 1/2007 | Goudie | |
| 2008/0091128 A1 | 4/2008 | Nan | |
| 2009/0005714 A1 * | 1/2009 | Mecenero | 601/46 |
| 2010/0013610 A1 | 1/2010 | Schwieger | |
| 2013/0116503 A1 | 5/2013 | Mertens et al. | |

OTHER PUBLICATIONS

International Search Report and Written Opinion mailed by the International Searching Authority on Feb. 20, 2015, for International Application No. PCT/US2014/066971.

* cited by examiner

*Primary Examiner* — John Lacyk
(74) *Attorney, Agent, or Firm* — Litts Law Firm

(57) ABSTRACT

A personal massager comprises a housing having a front end and a back end. A motor is mounted within the housing, and a crank is configured to move in a circular path within the housing when actuated by the motor. A rocker arm having a first end and a second end is rotatably coupled at a first location to the housing. An armature having a first end and a second end is rotatably coupled at a first location to the crank, and is rotatably coupled at a second location to a second location on the rocker arm. The armature may also be rotatably coupled at a third location to a third location on the rocker arm. A massage head is coupled to the first end of the armature.

34 Claims, 25 Drawing Sheets

PERSONAL MASSAGER

TECHNICAL FIELD

The present invention relates to personal massagers, and more particularly to a personal massager utilizing an armature and rocker arm assembly to generate motion in a massage head.

BACKGROUND

Personal massagers provide a safe, therapeutic, and sanitary mechanism for relieving discomfort and stimulating parts of the body. Existing personal massagers are available in various shapes and sizes, and generate various types of motion. One drawback of many existing personal massagers, however, is that they typically produce an unnatural motion that is unlike any form of human contact. Moreover, existing personal massagers often have shapes and textures that do not resemble any part of the human body. The artificial stimulation provided by these massagers does not accurately reproduce the therapeutic and pleasurable sensations generated by physical contact with another human. Consequently, efforts have been made to create personal massagers that more accurately simulate actual human contact.

One personal massage device that attempts to simulate human contact is disclosed in U.S. Pat. No. 3,978,851, to Sobel. Sobel discloses several variations of a massaging apparatus that includes a stroking device and a remote power pack. One of the disclosed stroking tools is a clasping-type "mouth" that is formed from a stationary jaw portion and a movable jaw portion. The therapeutic benefits of such an unnatural clasping motion, however, appear to be limited.

Another device, disclosed in U.S. Pat. No. 5,470,303, to Leonard et al., discloses a massage device that includes a housing and a tongue-shaped massage head. Motion is generated by an arcuate rod that rotates within a sleeve formed in the massage head. While the massage head attempts to reproduce the shape and texture of a human tongue, the distortions in the massage head created by the rotating movement of the arcuate rod do not accurately simulate the natural movements of a tongue.

U.S. Pat. No. 5,460,597, to Hopper, discloses a portable vibratory stimulator that includes a stationary housing having a simulated mouth on its front end and a moveable simulated tongue projecting from the mouth. The tongue is capable of a wide range of motion, but it is driven by a complicated arrangement of metal guides, pivot pins, and rings. Moreover, three separate motors actuated by multiple switches are required to generate motion in the simulated tongue. The use of multiple switches makes the device disclosed by Hopper difficult to operate with one hand, and the use of multiple motors and complex mechanical structures undesirably increases the weight of the device.

Accordingly, there remains a need for a personal massager that more accurately simulates human physical contact.

SUMMARY

One embodiment of the present invention is directed to a personal massager comprising a housing having a front end and a back end. A motor may be mounted within the housing, and a crank may be configured to move in a circular path within the housing when actuated by the motor. A rocker arm having a first end and a second end may be rotatably coupled at a first location on the rocker arm to the housing. An armature having a first end and a second end may be rotatably coupled at a first location to the crank, and may be rotatably coupled at a second location to a second location on the rocker arm. The armature may also be rotatably coupled at a third location to a third location on the rocker arm. A massage head may be configured to be coupled to the first end of the armature.

A gear drive may be housed within the housing, and may be configured to be actuated by the motor. The gear drive may comprise a first gear coupled to a motor shaft extending from the motor, and a second gear coupled to an axle that is mounted within the housing. The first gear and the second gear may be mounted within the housing in such a manner that the first gear meshes with the second gear. The crank may be coupled to the second gear. In one embodiment, the first gear may comprise a worm, and the second gear may comprises a worm gear. Preferably, the motor the motor of this embodiment comprises a standard DC motor. In another embodiment, the first gear may comprise a bevel pinion gear, and the second gear may comprise a bevel gear. Preferably, the motor of this embodiment comprises a gear motor.

The armature may comprise an armature body having a first end and a second end. The armature body may be configured to be coupled to the massage head. In one embodiment, the armature body may comprise a concave top surface, first and second convex side surfaces, a flat bottom surface, a rounded tip, and a flat back surface. A first concave groove may be formed in the first convex side surface, and a second concave groove may be formed in the second convex side surface. The armature may also comprise a first arm and a second arm. The first arm may have a first end and a second end. The first end of the first arm may be coupled to the second end of the armature body. A first hole may be formed in the first arm of the armature near its second end. The first hole may be configured to receive the crank. The second arm may have a first end and a second end. The first end of the second arm may be coupled to the second end of the armature body.

The rocker arm may comprise a cylindrical base having a first end and a second end. A first arm may be orthogonally coupled at its first end to the first end of the cylindrical base. A first projection may be coupled to the second end the first arm. The first projection may be configured to be received into a second hole formed in the first arm of the armature between its first end and the first hole. A second arm may be coupled at its first end to the second end of the cylindrical base. A second projection may be coupled to the second end of the second arm. The second projection may be configured to be received into a third hole formed in the second arm of the armature near its second end. Preferably, the third hole formed in the second arm of the armature is coaxial with the second hole formed in the first arm of the armature. The rocker arm may be rotatably coupled to the housing by positioning the cylindrical base of the rocker arm between a semi-cylindrical groove formed in a rocker arm support extending forward from the front end of the housing and a semi-cylindrical groove formed in a rocker cap, and coupling the rocker cap to the rocker arm support.

The first end of the armature may extend through an opening formed in the front end of the housing, and the second end of the armature may be supported within the housing. The massage head may comprise a massage head body having a front end and a back end. The massage head body may be configured to be coupled to the first end of the armature. Preferably, a cavity configured to tightly house the armature body is formed in the massage head body. The massage head may further comprise a tubular wall extending backward from the back end of the massage head body. The tubular wall may be configured to be coupled to the front end of the housing. In one embodiment, an internal flange is formed near the back end of the tubular wall. The internal flange may be configured to be received into an external groove formed near the front end of the housing. At least one ridge may be formed around the outer surface of the tubular wall near its back end. Preferably, at least one corrugation is formed in the tubular wall.

A three-way rocker switch may be affixed to the housing, and may be configured to control electrical communication between a power supply and the motor. The three-way rocker switch may comprise a first terminal, a second terminal, and a third terminal. In one embodiment, the first terminal of the three-way rocker switch is electrically coupled to a first terminal of the motor, the second terminal of the three-way rocker switch is electrically coupled to a first terminal of the power supply, the first terminal of the three-way rocker switch is electrically coupled to the third terminal of the three-way rocker switch through a diode, and a second terminal of the motor is coupled to a second terminal of the power supply.

The crank may be configured to move in a circular path that defines a first plane when actuated by the motor. The first end of the armature may be configured to move in a closed plane path that defines a second plane when the crank moves in its circular path. Preferably, the first plane defined by the circular path of the crank is parallel to the second plane defined by the closed plane path of the first end of the armature.

BRIEF DESCRIPTION OF THE DRAWINGS

Various embodiments of the invention are described in the following detailed description with reference to the accompanying drawings, in which.

DETAILED DESCRIPTION

A personal massager and its method of manufacture are described herein. The specific details set forth in the following description provide an understanding of certain embodiments of the invention, and do not limit the scope of the invention as set forth in the claims. Certain structures and steps that are well known in the art are not described in detail. Reference is made in the following description to the accompanying drawings. Wherever possible, the same reference numbers are used throughout the drawings and the corresponding description to refer to the same or similar structures or steps.

Figure 1:
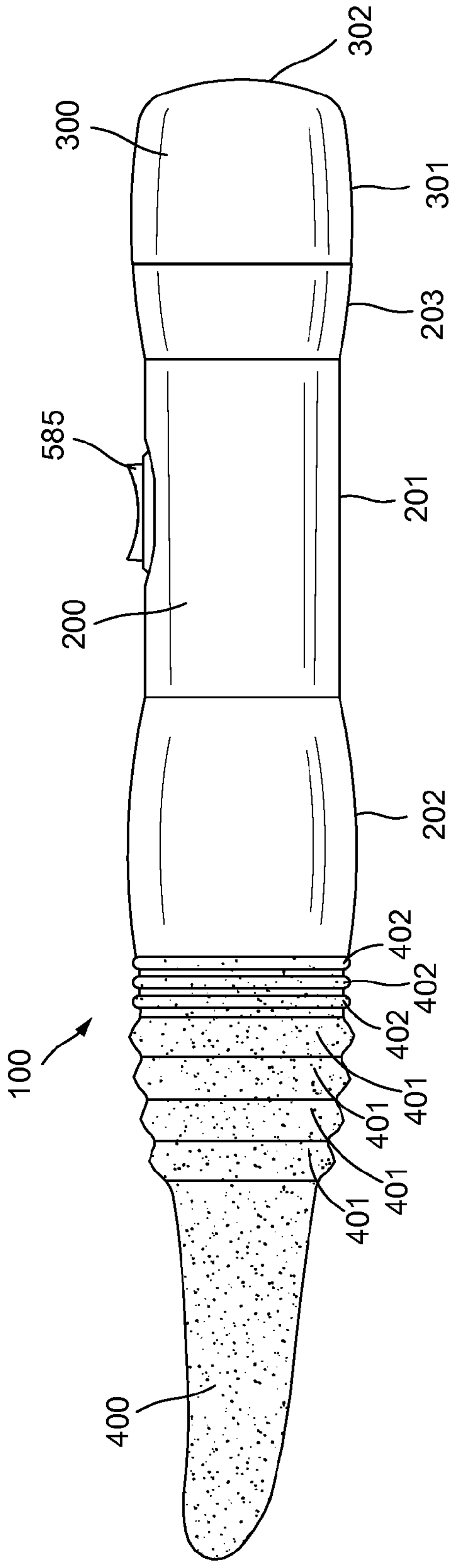
FIG. 1 is a side view of a personal massager in accordance with one embodiment of the present invention.
Figure 2:
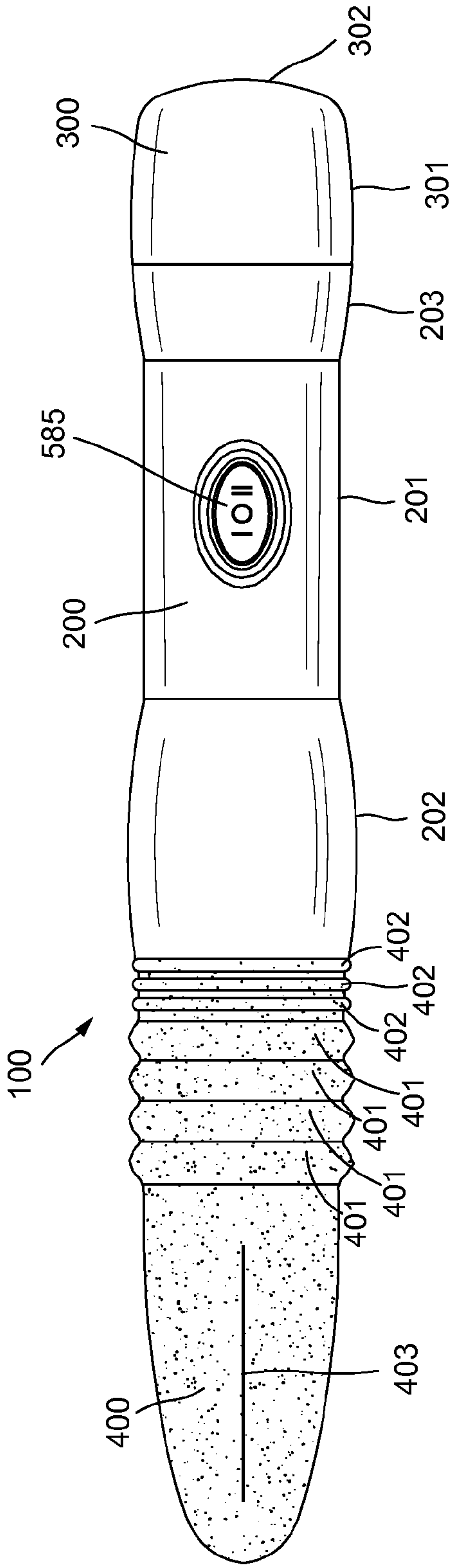
FIG. 2 is a top view of the personal massager of FIG. 1.

FIGS. 1 to 2 show a personal massager 100 in accordance with one embodiment of the present invention. The personal massager 100 may comprise a housing 200, a battery cap 300, and a massage head 400. The housing 200 and battery cap 300 may be formed of a relatively rigid and lightweight material such as high-density polyethylene, and the massage head 400 may be formed of a relatively soft and flexible material such as silicone rubber. Preferably, the massage head 400 is detachably coupled to the front end of the housing 200, and the battery cap 300 is detachably coupled to the back end of the housing 200, as shown in FIGS. 1 to 2. A switch 585 may be affixed to the top surface of the housing 200.

In the configuration shown in FIGS. 1 to 2, the housing 200 has a straight cylindrical outer side surface 201 near its midpoint, bulging outward towards either end to form a first cylindrical protrusion 202 and a second cylindrical protrusion 203. The massage head 400 may be coupled to the housing 200 in such a manner that its outer surface extends forward from the front end of the first cylindrical protrusion 202. One or more corrugations 401 may be formed along the length massage head 400, and one or more ridges 402 may be formed around the outside surface of the massage head 400 near its point of attachment with the housing 200. The battery cap 300 may be coupled to the housing 200 in such a manner that its outer surface extends backward from the back end of the second cylindrical protrusion 203. The battery cap 300 may have a cylindrical outer side surface 301 and an outer end surface 302 which, in combination with the second cylindrical protrusion 203, form a knob at the back end of the personal massager 100. The switch 585 may be affixed to the housing 200 between the first cylindrical protrusion 202 and the second cylindrical protrusion 203.

The housing 200 is preferably configured to house a power supply and a drive mechanism that may include a motor, a gear drive, a crank, a rocker arm, and an armature. The crank may be configured to move in a circular path within the housing 200. The crank may be coupled, either directly or indirectly, to one of the gears in the gear drive. A rocker arm may be rotatably coupled, either directly or indirectly, to the housing 200. In some embodiments, the rocker arm is rotatably coupled to a rocker arm support that extends forward from the front end of the housing 200. The rocker arm support may be formed integrally with the housing 200, or may be a separate component that is coupled to the housing 200. An armature may be rotatably coupled at a first location to the crank, and at a second location to the rocker arm, such that at least a portion of its second end is supported within the housing 200, with at least a portion of its first end protruding through an opening formed at the front end of the housing 200. Preferably, the first end of the armature is coupled to the massage head 400, so that any motion in the first end of the armature is translated to the massage head 400. In the preferred configuration, when the switch 585 is switched to an "on" position, the power supply provides electrical power to the motor, which actuates the gear drive and creates a circular motion in the crank that is imparted to the armature, thereby producing motion in the protruding end of the armature that follows a closed plane curve. This motion is mirrored by the massage head.

The size, shape, and configuration of the housing 200 may be selected to accommodate the various components housed therein. In particular, certain gear drive configurations may require larger motors that necessitate a larger housing, whereas other gear drive configurations may work with smaller motors that can be accommodated by a smaller housing. Similarly, different configurations of the crank, rocker arm, and armature may require varying amounts of space to accommodate their movements when the personal massager is powered "on." Additionally, different motors may require that different mounting structures be formed within the interior of the housing 200. Moreover, the size and shape of the housing 200 may reflect various ergonomic and aesthetic design considerations. Accordingly, the housing 200 is not limited to any particular size, shape, or configuration.

Figure 3:
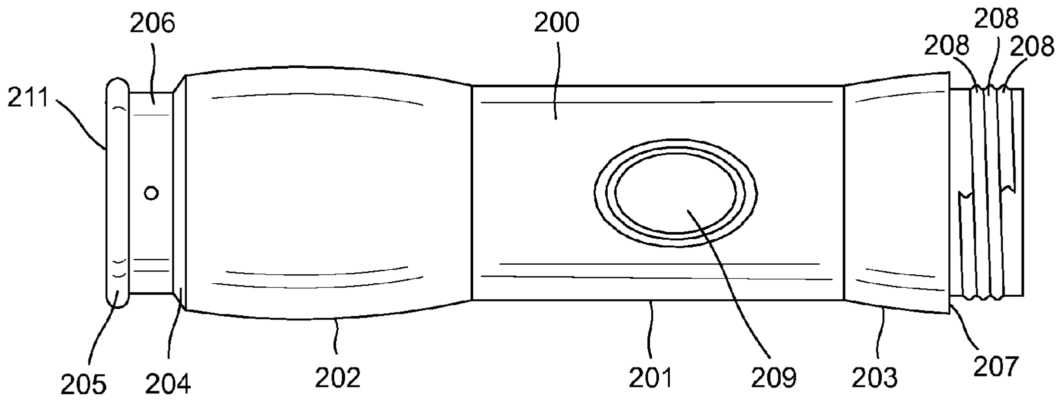
FIG. 3 is a top view showing the exterior of a housing in accordance with one embodiment of the present invention.
Figure 4:
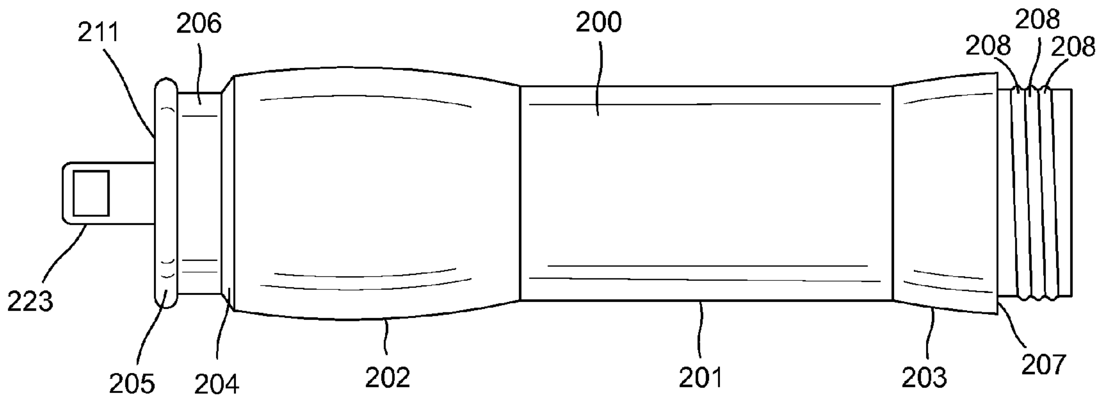
FIG. 4 is a bottom view showing the exterior of the housing of FIG. 3.
Figure 5:
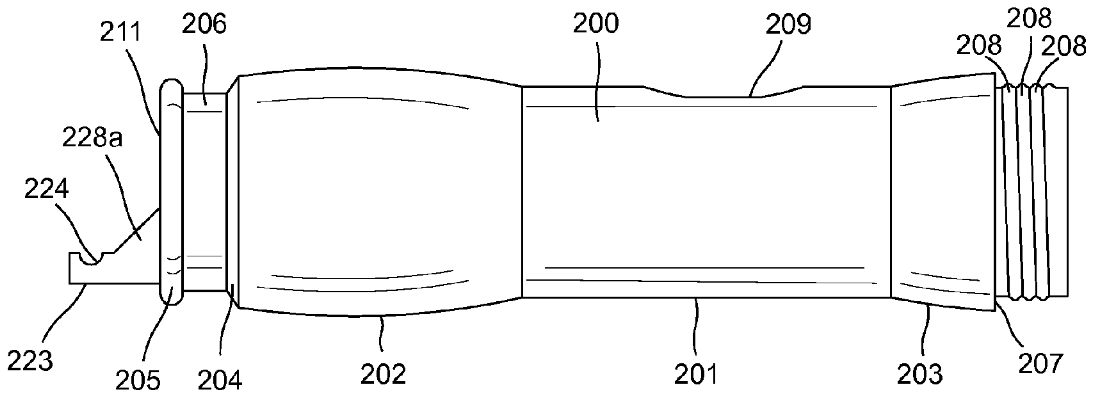
FIG. 5 is a side view showing the exterior of the housing of FIG. 3.
Figure 6:
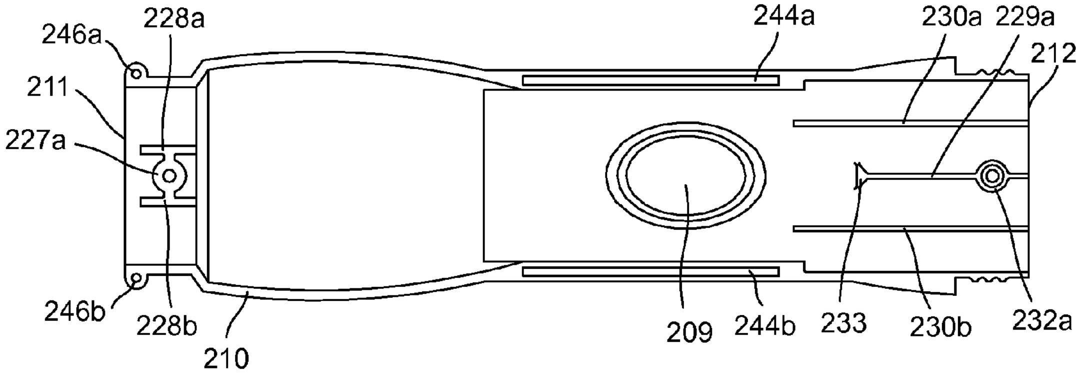
FIG. 6 is a bottom view showing an upper housing portion in accordance with one embodiment of the present invention.
Figure 7:
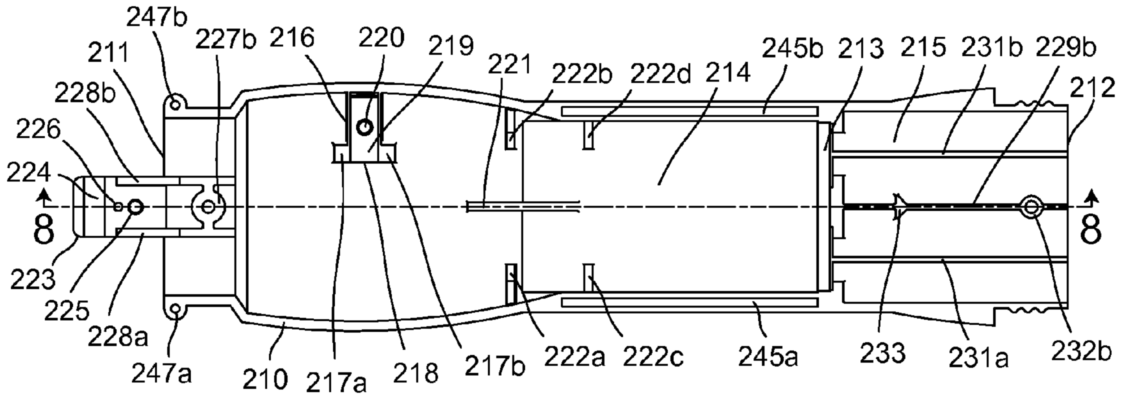
FIG. 7 is a top view showing a lower housing portion in accordance with one embodiment of the present invention.
Figure 8:
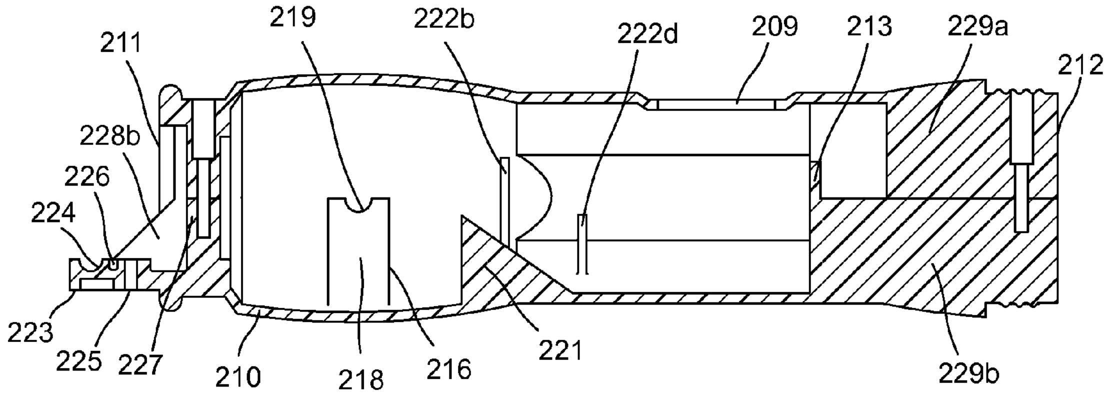
FIG. 8 is a cross-sectional view through a vertical plane showing the interior of the housing of FIG. 3.

The housing 200 of the embodiment shown in FIGS. 1 to 2 is suitable for a configuration in which the gear drive comprises a worm and a worm gear, and the motor is a standard DC motor. The exterior of the housing 200 of this embodiment is shown in FIGS. 3 to 5, and the interior is shown in FIGS. 6 to 8. Referring to FIGS. 3 to 5, the first cylindrical protrusion 202 may terminate at a first annular wall 204 encircling the housing 200. An external flange 205 may be formed around the outer surface of the housing 200 at or near its front end, thereby defining a groove 206 between the flange 205 and the first annular wall 204. The second cylindrical protrusion 203 may terminate at a second annular wall 207 encircling the housing 200. External threads 208 may be formed around the outer surface of the housing 200 between the second annular wall 207 and the back end. A hole 209 may be formed through the housing 200 between the first cylindrical protrusion 202 and the second cylindrical protrusion 203 to accommodate the switch 585.

Referring to FIGS. 6 to 8, the housing 200 may comprise a generally cylindrical wall 210 of varying diameter and thickness along its length, terminating at either end to form front and back circular openings 211 and 212. A vertical partition 213 may extend transversely along a portion of the inside surface of the housing 200, thereby defining a drive mechanism chamber 214 and a power supply chamber 215. The drive mechanism chamber 215 may be configured to house the motor and the gear drive, and preferably provides sufficient space to allow for the circular motion of the crank and the resulting motion in the rocker arm and armature. The power supply chamber 215 may be configured to house a power supply such as a pair of alkaline batteries, a rechargeable battery pack, or an AC/DC adapter.

Figure 9:
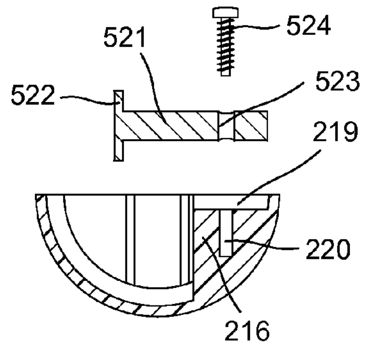
FIGS. 9 and 10 are cross-sectional views through a vertical plane showing an axle, axle support, and thread-forming screw in accordance with one embodiment of the present invention.

An axle support 216 may be formed on, or attached to, the inner surface of the housing 200 within the drive mechanism chamber 215. Preferably, the axle support 216 is a T-shaped structure when viewed from above, having a pair of projections 217*a* and 217*b* that define a flat vertical surface 218 lying in a plane that is parallel to, and offset from, the axis of the housing 200. A semi-cylindrical groove 219 may be formed transversely through the horizontal top surface of the axle support 216, and a non-threaded hole 220 may be formed through the groove 219 and into the axle support 216, as shown in FIGS. 7, 8, and 9.

A lower motor support 221 may be formed on, or attached to, the inner surface of the housing 200, preferably coplanar with the axis of the housing 200. Preferably, the lower motor support 221 has a top edge that is inclined relative to the axis of the housing 200. With this configuration, the lower motor support 221 can support a motor at an incline such that a gear attached to the motor shaft, such as a worm or a pinion, meshes with another gear in the gear drive. Side motor supports 222*a*, 222*b*, 222*c*, and 222*d* may also be transversely formed on, or attached to, the inner surface of the housing 200. Preferably, the side motor supports 222*a*, 222*b*, 222*c*, and 222*d* are substantially perpendicular to the lower motor support 221, and terminate at vertical edges that are laterally offset from the lower motor support 221. The side motor supports 222*a*, 222*b*, 222*c*, and 222*d* may be configured to maintain a motor in a position such that its axis is coplanar with the axis of the housing 200.

A rocker arm support 223, shown in FIGS. 4, 5, 7, and 8, may project forward from the front end of the housing 200. The rocker arm support 223 may be formed integrally with, or attached to, the housing 200. Preferably, the midline of the rocker arm support 223 is coplanar with the axis of the housing 200. A semi-cylindrical groove 224 may be formed transversely through the top surface of the rocker arm support 223, and a non-threaded hole 225 may be formed vertically through the rocker arm support 224. Another cylindrical or semi-circular hole 226 may be formed through the top surface of the rocker arm support 223, preferably between the groove 224 and the non-threaded hole 225. A front column 227, which is preferably cylindrical, may be formed vertically across the diameter of the housing near the front circular opening 211. Gussets 228*a* and 228*b* may be coupled to both the rocker arm support 223 and the front column 227, thereby providing structural support for the rocker arm support 223.

The power supply chamber 215 may be configured to house a pair of batteries. A power supply chamber divide 229 may be formed vertically within the power supply chamber 215 across the diameter of the housing 200. In some embodiments, the upper half of the power supply chamber divide 229*a* may extend only partway across the length of power supply chamber 215, whereas the lower half of the divide 229*b* may extend across the full length of the chamber 215, as shown in FIG. 8. Upper battery supports 230*a* and 230*b*, and lower battery supports 231*a* and 231*b*, may be formed along the inner surface of the housing 200 on either side of the power supply chamber divide 229, as shown in FIGS. 6 and 7. A back column 232, which is preferably cylindrical, may be formed vertically across the diameter of the housing 215, bisecting the power supply chamber divide 231. A middle column 233, which is preferably triangular in shape, may be formed between the vertical partition 213 and the back column 232. The middle column 233 may be formed at the terminal vertical edge of the upper half of the power supply chamber divide 229*a*, and may further bisect the lower half of the power supply chamber divide 229*b*.

Figure 18A:
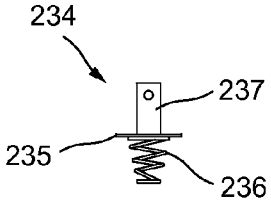
FIGS. 18*a* to 18*c* are top, end, and side views of a spring contact in accordance with one embodiment of the present invention.
Figure 18B:
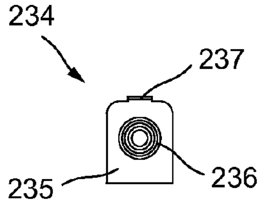
Figure 18C:
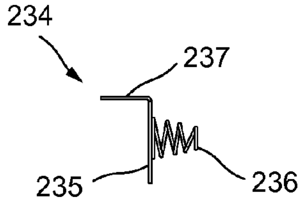
Figure 19:
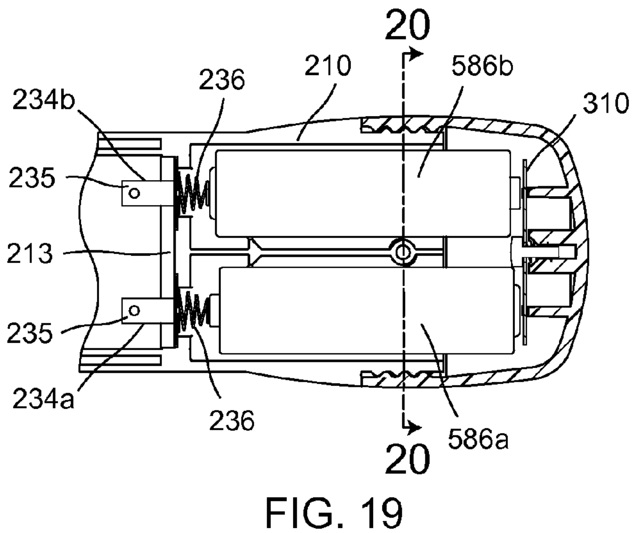
FIG. 19 is a partial cross-sectional view through a horizontal plane showing a housing, a battery cap, and a pair of batteries in accordance with one embodiment of the present invention.
Figure 20:
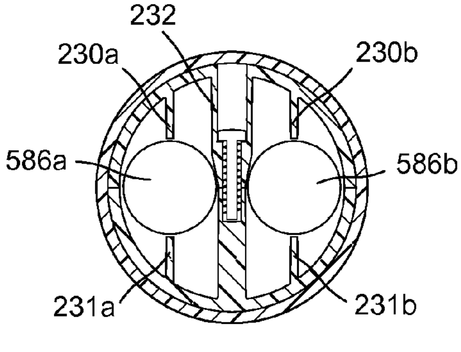
FIG. 20 is a partial cross-sectional view through a vertical plane showing a housing, a battery cap, and a pair of batteries in accordance with one embodiment of the present invention.

FIGS. 19 and 20 show a pair of batteries 586*a* and 586*b* housed within the power supply chamber 215. The batteries 586*a* and 586*b* shown are a pair of AA alkaline batteries, although any other number, type, and size of batteries may be used. A pair of spring contacts 234*a* and 234*b*, such as those shown in FIGS. 18*a* to 18*c*, may be attached to the vertical partition 213. Each spring contact 234 may include a plate 235, a spring coil 236 for making electrical contact with a terminal of a battery 586, and a tab 237 that can be bent at a ninety degree angle with respect to the plate 235. The spring contacts 234*a* and 234*b* are preferably mounted on the vertical partition 213 such that the spring coils 234 extend into the power supply chamber 215, and the tabs 237 extend into the drive mechanism chamber 214, as shown in FIG. 19.

Figure 15:
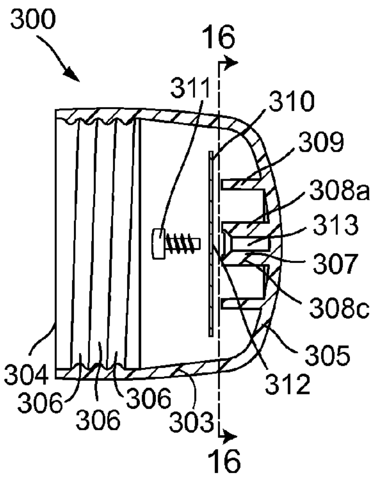
FIGS. 15 to 17 are cross-sectional views through a vertical plane showing a battery cap in accordance with one embodiment of the present invention.
Figure 16:
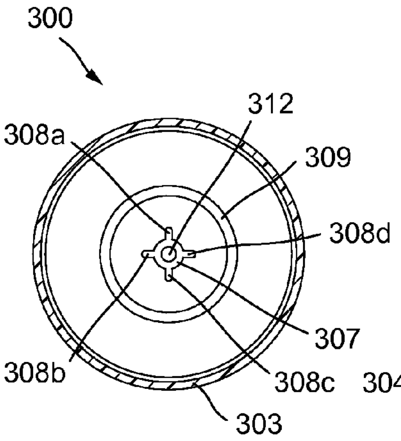
Figure 17:
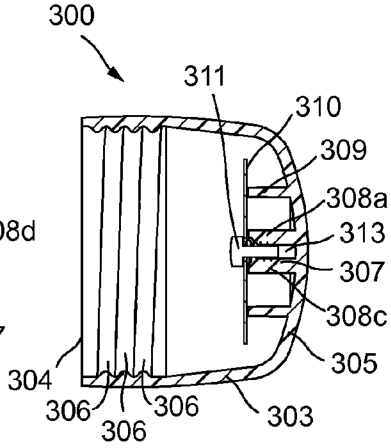

The back circular opening 212 of the of the housing 200 may be enclosed by the battery cap 300, which may be screwed onto the back end of the housing 200, as shown in FIG. 19. FIGS. 15 to 17 show a battery cap 300 that is suitable for use with the housing shown in FIGS. 3 to 8. The battery cap 300 may comprise a generally cylindrical wall 303 of varying diameter and thickness, terminating at its front end at a front circular opening 304, and at its back end at a back wall 305. Internal threads 306 may be formed near the front circular opening 304 of the battery cap 300, and may be configured to mesh with the external threads formed near the back circular opening 212 of the housing 200. The inner surface of the cylindrical wall 303 near its front circular opening 304 may have a slightly larger diameter as the outer surface of the housing 200 near its back circular opening 212, thereby allowing the front end of the cylindrical wall 303 to be screwed over the back end of the housing 200. A column 307 may extend horizontally inward from the center of the back wall 305, and may be reinforced by one or more gussets 308*a*, 308*b*, 308*c*, and 308*d*. A cylindrical disc support 309, which preferably terminates in the same vertical plane as the column 307, may extend inward from the back wall 305 and surround the column 307. A contact disc 310 may be coupled to the column 307 by screwing a thread-forming screw 311 through a hole 312 in the contact disc 310 and into a non-threaded hole 313 formed through the axis of the column 307.

Screwing the battery cap 300 onto the back end of the housing 200 may cause the batteries 586*a* and 586*b* to come into electrical contact with the spring contacts 234*a* and 234*b* and the contact disc 310. The disc support 309 may function to prevent the contact disc 310 from deforming as a result of pressure from the batteries 586*a* and 586*b*. Variations in the structure and configuration of the power supply chamber 215 and the battery cap 300 may be made to accommodate different types of power supplies. In some embodiments, such as those using an AC motor, the power supply chamber 215 may be omitted. Furthermore, in some embodiments, the battery cap 300 may be omitted, in which case the housing may terminate at a back wall (not shown) rather than at a back circular opening 212.

In some embodiments, the housing 200 may comprise an upper housing portion 238 and a lower housing portion 239, as shown in FIGS. 11 to 14. In such embodiments, the cylindrical wall 210, as well as a number of other components of the housing 200, such as the front, middle, and back columns 227, 232, and 233, the gussets 228*a* and 228*b*, and the power supply chamber divide 229, may be divided into upper and lower portions. The upper and lower housing portions 238 and 239 may be coupled to each other by screwing thread-forming screws 240 and 241 through non-threaded holes 242*a* and 243*a* formed in the upper front and upper back columns 227*a* and 232*a*, and into coaxially-formed non-threaded holes 242*b* and 243*b* formed in the lower front and lower back columns 227*b* and 232*b*. In other embodiments, different techniques for coupling the upper and lower housing portions 238 and 239 may be used. For example, in some embodiments, an adhesive may be applied between the mating surfaces of the upper and lower housing portions 238 and 239 to bond them together.

To facilitate alignment of the upper and lower housing portions 238 and 239, ridges 244*a* and 244*b* (shown in FIGS. 6, 13, and 14), which are preferably semi-cylindrical, may be formed along at least a portion the length of the horizontal edges of the upper housing portion 238. These ridges 244*a* and 244*b* may be configured to mate with corresponding grooves 245*a* and 245*b* (shown in FIGS. 7, 13, and 14) formed along the horizontal edges of the lower housing portion 239. Similarly, protrusions 246*a* and 246*b* (shown in FIG. 6), which are preferably semi-circular, may be formed in the horizontal edges of the upper housing portion 238 and configured to mate with corresponding grooves 247*a* and 247*b* (shown in FIG. 7) formed in the horizontal edges of the lower housing portion 239. Mating of the ridges 244*a* and 244*b*, and protrusions 246*a* and 246*b*, with the corresponding grooves 245*a*, 245*b*, 247*a*, and 247*b*, maintains alignment between the upper and lower housing portions 238 and 239 when they are coupled to one another.

Figure 21:
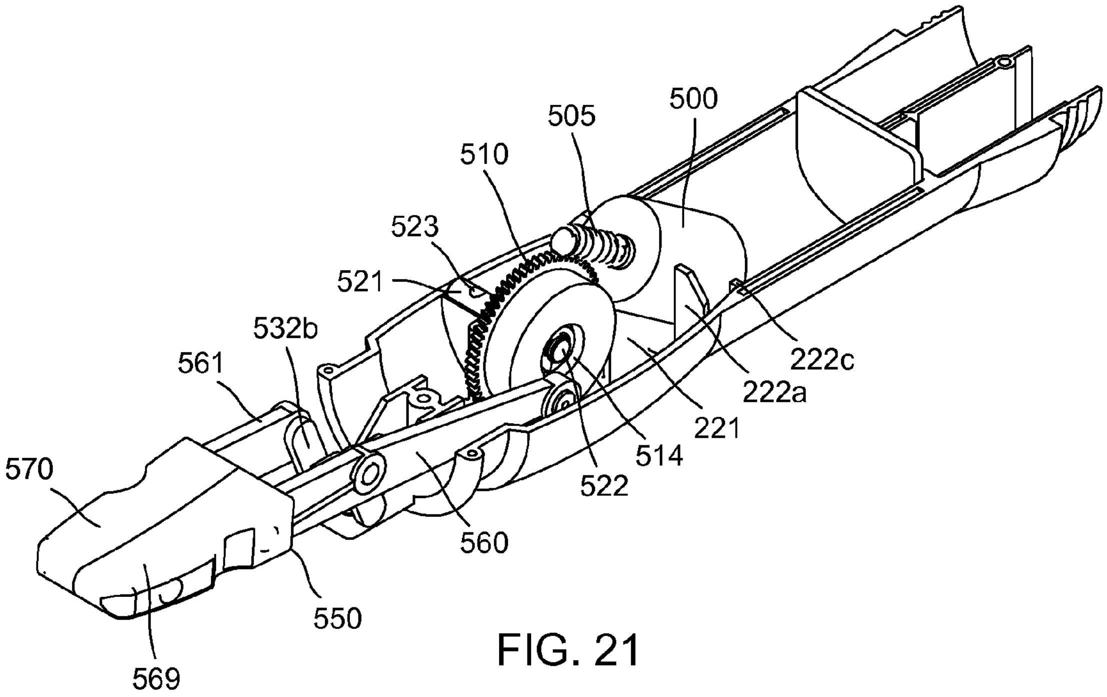
FIG. 21 is a perspective view showing a lower housing portion and a drive mechanism in accordance with one embodiment of the present invention.
Figure 22:
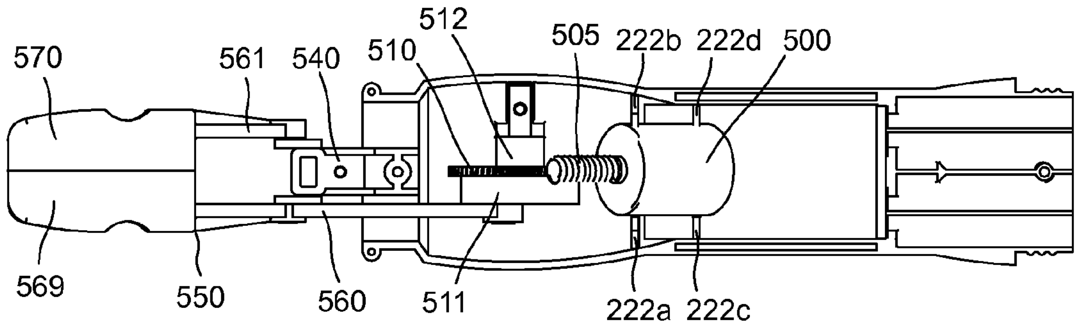
FIG. 22 is a top view showing a lower housing portion and a drive mechanism in accordance with one embodiment of the present invention.
Figure 23:
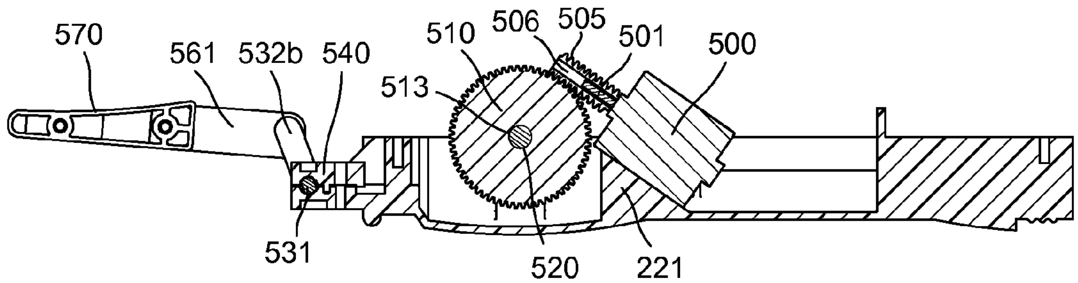
FIG. 23 is a cross-sectional view through a vertical plane showing a lower housing portion and a drive mechanism in accordance with one embodiment of the present invention.
Figure 24:
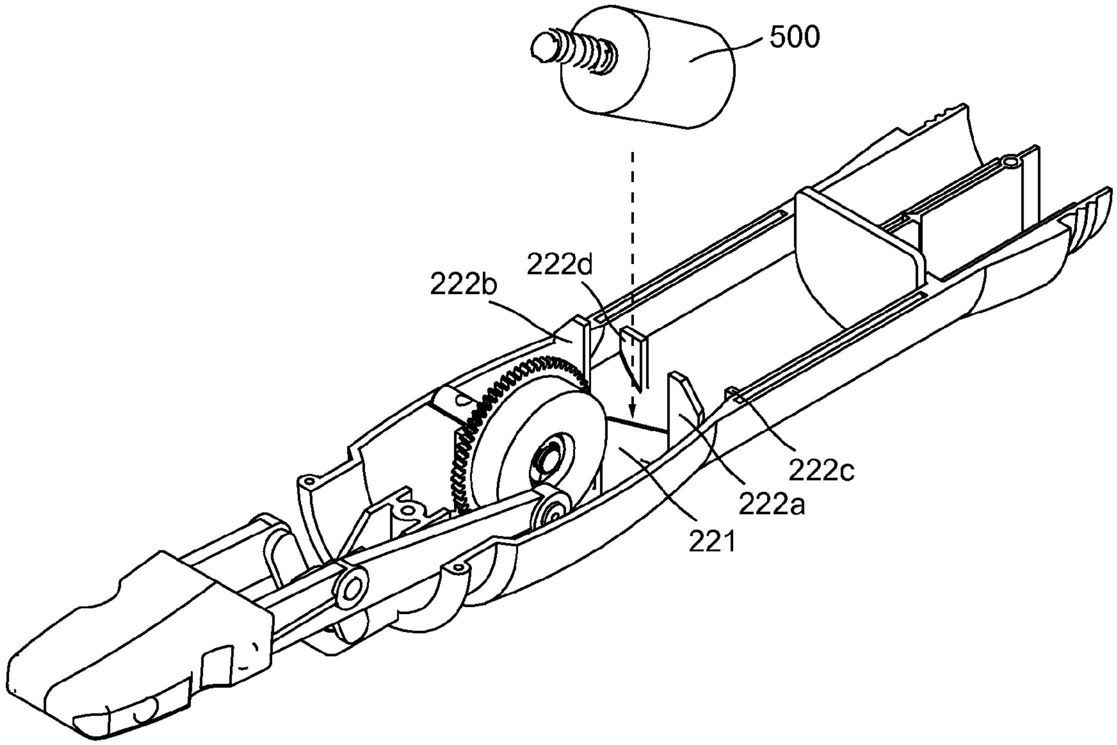
FIGS. 24 and 25 are perspective views showing the mounting of a motor within a lower housing portion in accordance with one embodiment of the present invention.
Figure 25:
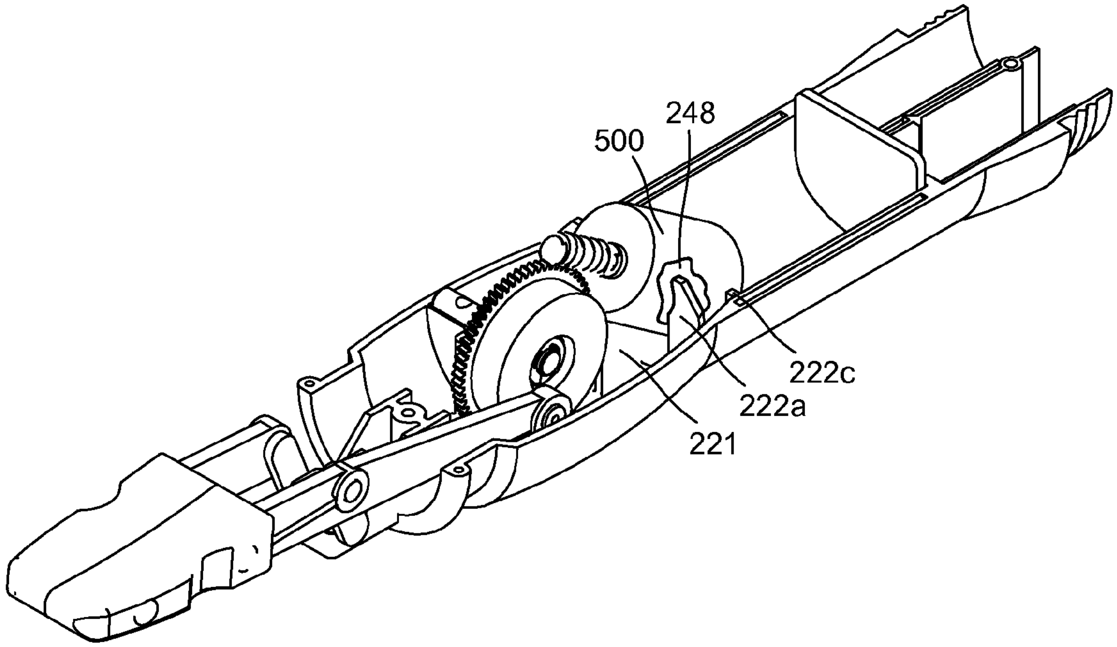
Figure 26:
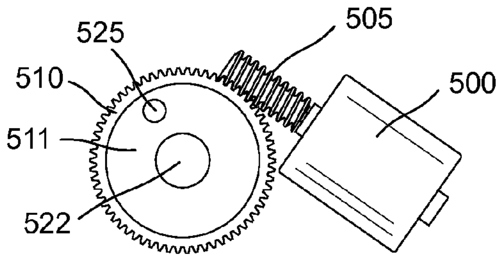
FIGS. 26 and 27 are side and top views of a drive mechanism in accordance with one embodiment of the present invention.
Figure 27:
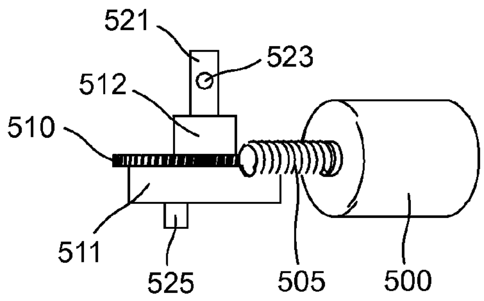
Figure 29:
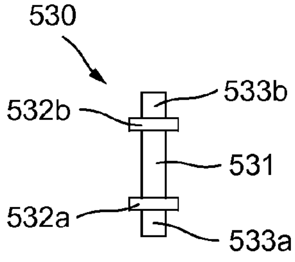
FIGS. 29 and 30 are top and front views of a rocker arm in accordance with one embodiment of the present invention.
Figure 30:
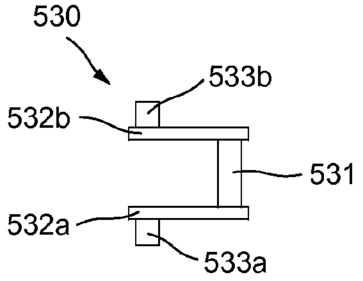

FIGS. 21 to 23 show a drive mechanism housed within the housing 200 of FIGS. 3 to 8. The drive mechanism of this embodiment may include a motor 500, a worm 505 affixed to the shaft 501 of the motor 500, a worm gear 510 mounted on an axle 520, a crank 525 (shown in FIGS. 26 to 27) coupled to a side of the worm gear 510, a rocker arm 530 (shown in FIGS. 29 to 30) rotatably coupled to the rocker arm support 223 by a rocker cap 540, and an armature 550 rotatably coupled to both the crank 525 and the rocker arm 530, thereby suspending the armature 550 partially within the housing 200. The gear drive of this embodiment, comprising the worm 505 and the worm gear 510, may provide a significant amount of gear reduction such that the rotational speed of the worm gear 510 is significantly less than that of the motor shaft 501. The motor 500 used the gear drive of this embodiment is preferably a standard DC motor, such as a SunTech model SU143 3 Volt DC motor. If a different gear drive is used, a different type of motor, such as a gear motor, may be used (instead of a standard DC motor) to provide any necessary gear reduction. The motor 500 may be mounted on the lower motor support 221 at an incline relative to the axis of the housing 200, as shown in FIG. 24, and may be maintained in lateral alignment by the side motor supports 222*a*, 222*b*, 222*c*, and 222*d*. The motor 500 may be affixed to the housing by applying hot melt adhesive 248 to at least one of the contact points between the motor 500 and the side motor supports 222*a*, 222*b*, 222*c*, and 222*d*, as shown in FIG. 25.

The shaft 501 of the motor 500 may be inserted into the bore 506 of the worm 505, thereby coupling the worm 505 to the shaft 501. The shaft 501 may have a key (not shown) that fits with a keyseat (not shown) in the bore 506, thereby preventing relative rotation between the shaft 501 and the worm 505. The motor 500 may be mounted in such a position, and at such an angle of inclination, that the thread of the worm 505 meshes with the teeth of the worm gear 510. The number of teeth on the worm gear 510 may be selected to achieve the desired gear reduction for the drive mechanism. A first cylindrical projection 511 may be formed on, or affixed to, one side of the worm gear 500, and a second cylindrical projection 512 may be formed on, or affixed to, the other side of the worm gear 500. Preferably, the first and second cylindrical projections 511 and 512 do not have teeth, and have outer diameters that are smaller than that of the worm gear 510. The length of the first and second cylindrical projections 511 and 512 can be selected to ensure that the thread of the worm 505 meshes with the teeth of the worm gear 510, and to ensure that the crank 525 securely engages the armature 550.

Figure 10:
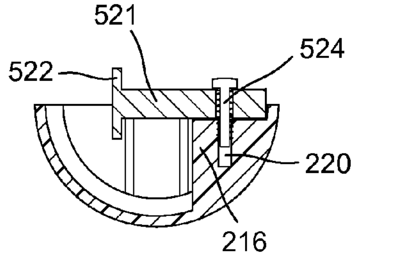
Figure 11:
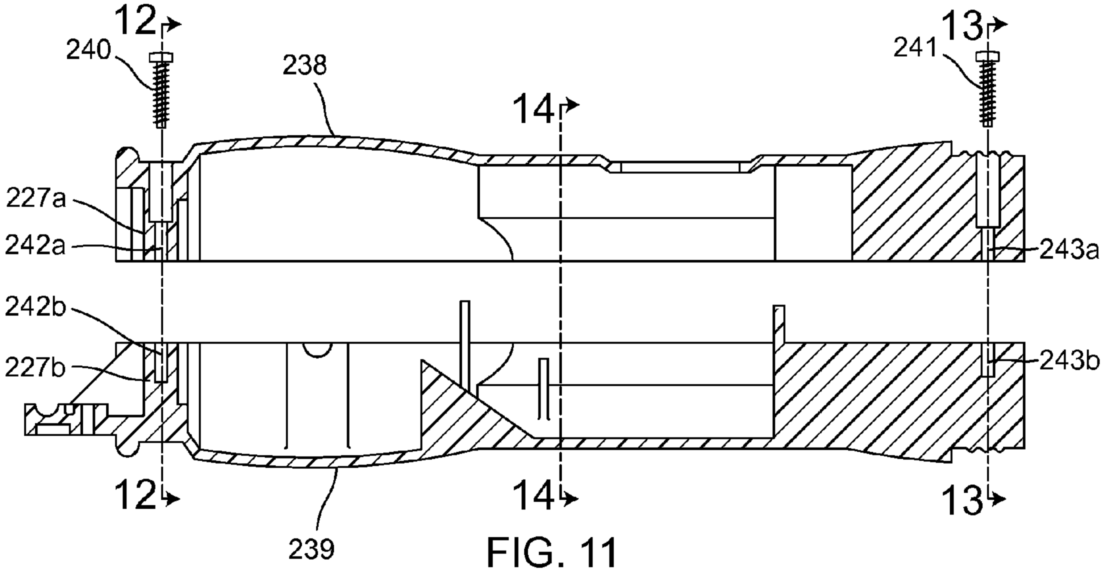
FIG. 11 is a cross-sectional views through a vertical plane showing upper and lower housing portions in accordance with one embodiment of the present invention.
Figure 12:
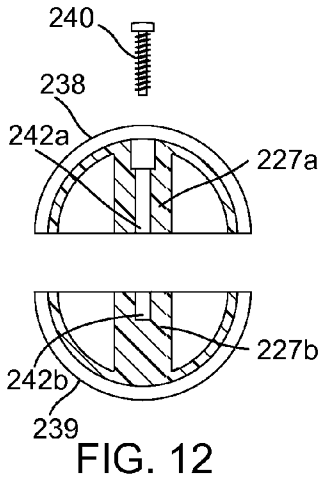
FIGS. 12 to 14 are cross-sectional views through a vertical plane showing the upper and lower housing portions of FIG. 11.
Figure 13:
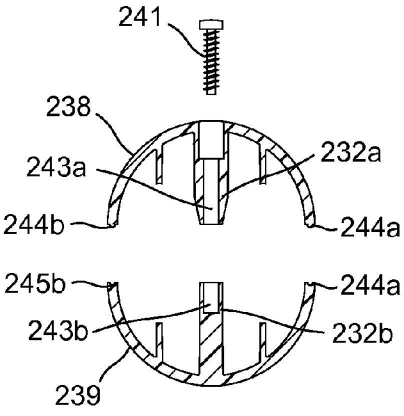
Figure 14:
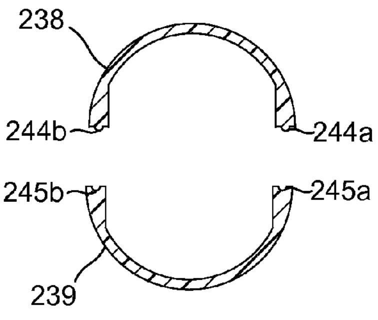
Figure 28:
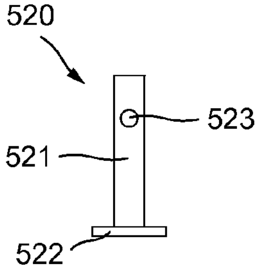
FIG. 28 is a top view of an axle in accordance with one embodiment of the present invention.

The worm gear 510 may be mounted on the axle 520, shown in FIG. 28, by inserting the axle shaft 521 through the bore 513 of the worm gear 510 and the first and second cylindrical projections 511 and 512. Preferably, the joint between the axle 520 and the worm gear 510 is not keyed, so that the worm gear 510 can rotate relative to the axle 520. A cylindrical recess 514 may be formed around the bore 513 at the exposed side surface of the first cylindrical projection 511 for receiving the head 522 of the axle 520. The axle 520 may be mounted on the axle support 216 by positioning the axle shaft 521 within the axle support groove 219, and screwing a thread-forming screw 524 through a hole 523 in the shaft 521 and into the non-threaded hole 220 in the axle support 216, as shown in FIGS. 9 to 10. The exposed side surface of the second projection 512 may abut the flat vertical surface 218 of the axle support 216 when the worm gear 510 is mounted on the axle 520, and the axle 520 is mounted on the axle support 216. The crank 525, which is preferably cylindrical, may be mounted eccentrically with respect to the axle 520 on the exposed side surface of the first cylindrical projection 512.

The rocker arm 530 may be configured so that it can be rotatably coupled at a first location (preferably at or near its first end) to the housing 200 and at a second location (preferably at or near its second end) to the armature 550. Optionally, the rocker arm 530 may also be configured so that it can be rotatably coupled at a third location (preferably at the same distance along the length of the armature as the second location) to the armature 550. One embodiment of the rocker arm 530, shown in FIGS. 29 and 30, comprises a cylindrical base 531, first and second arms 532*a* and 532*b* orthogonally coupled near their first ends to opposite ends of the base 531, and first and second projections 533*a* and 533*b* coupled to sides of the arms 532*a* and 532*b* near their second ends. The first ends of the first and second arms 532*a* and 532*b* define the first end of the rocker arm 530, and the second ends of the arms 532*a* and 532*b* define the second end of the rocker arm 530. Preferably, the first and second arms 532*a* and 532*b* are parallel to each other and of equal length, and the first and second projections 533*a* and 533*b* are coaxially attached to outward-facing side surfaces of the arms 532*a* and 532*b*, respectively. The cylindrical base 531 may provide the means for rotatably coupling the rocker arm 530 at a first location to the housing 200. The first and second projections 533*a* and 533*b* may provide the means for rotatably coupling the rocker arm 530 at second and third locations to the armature 550.

Figure 31:
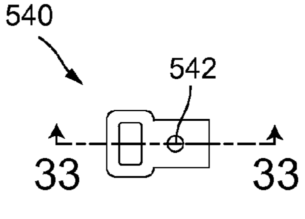
FIGS. 31 and 32 are top and side views of a rocker cap in accordance with one embodiment of the present invention.
Figure 32:
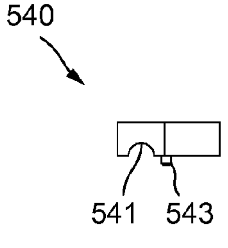
Figure 33:
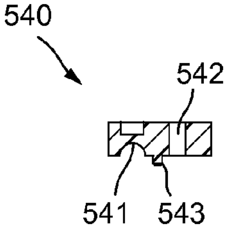
FIG. 33 is a cross-sectional view through a vertical plane showing the rocker cap of FIGS. 31 and 32.
Figure 34:
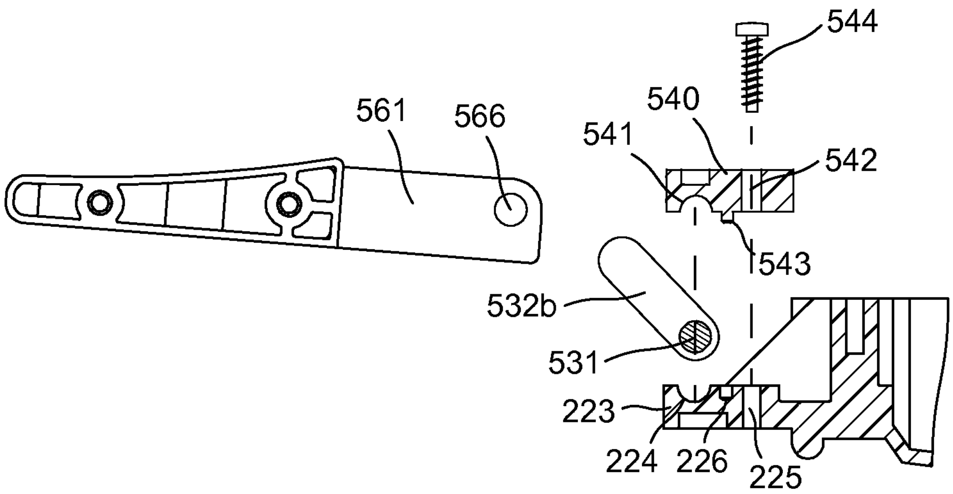
FIGS. 34 and 35 are partial cross-sectional views through a vertical plane showing the mounting of a rocker arm and an armature onto a rocker arm support via a rocker cap in accordance with one embodiment of the present invention.
Figure 35:
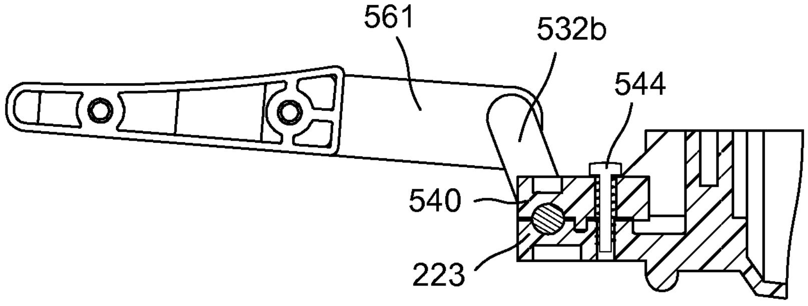
Figure 36A:
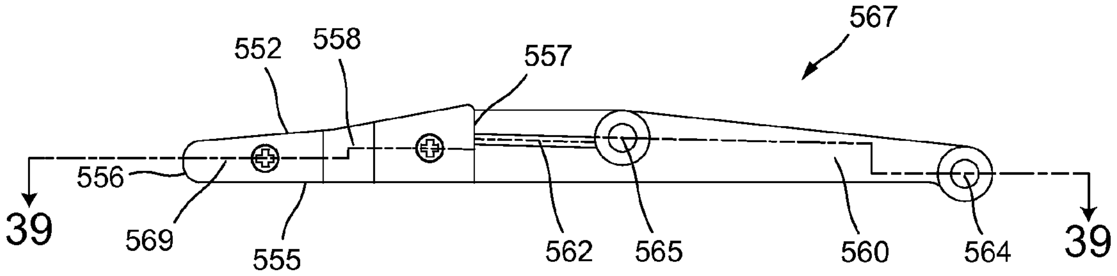
FIGS. 36*a* and 36*b* are side views of a first armature portion in accordance with one embodiment of the present invention.
Figure 36B:
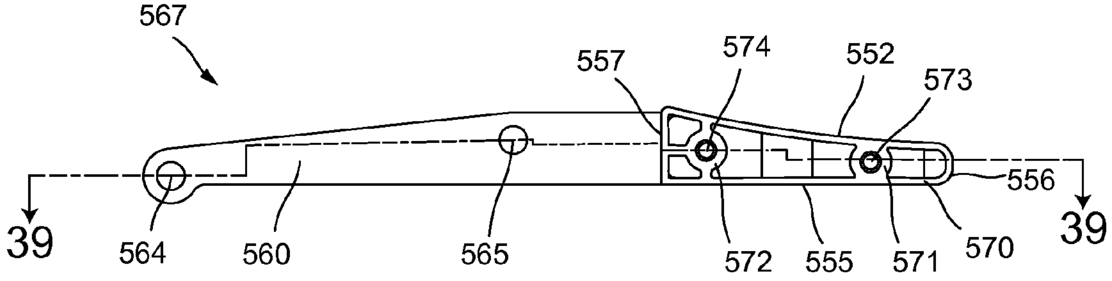
Figure 37A:
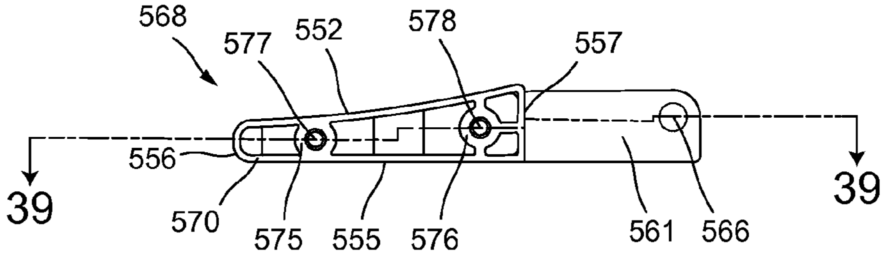
FIGS. 37*a* and 37*b* are side views of a second armature portion in accordance with one embodiment of the present invention.
Figure 37B:
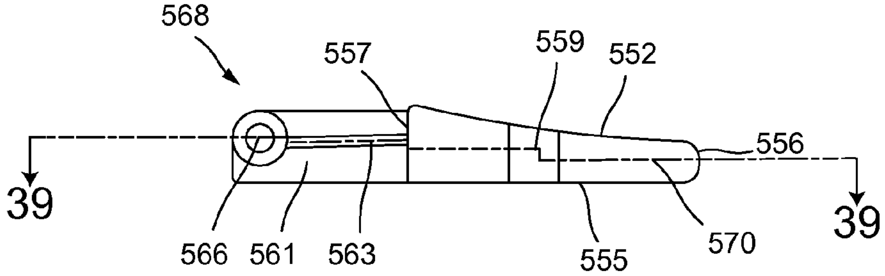

The rocker cap 540, shown in FIGS. 31 to 33, may be used to rotatably couple the first end of the rocker arm 530 to the housing 200. A semi-cylindrical groove 541 may be formed transversely through the bottom horizontal surface of the rocker cap 540, and a non-threaded hole 542 may be formed vertically through the rocker cap 540. A cylindrical or semicircular projection 543 may extend downward from the bottom surface of the rocker cap 540, preferably between the groove 541 and the hole 542. The rocker arm 530 may be rotatably coupled to the housing 200 by positioning the cylindrical base 531 within the semi-cylindrical groove 224 of the rocker arm support 223, and placing the rocker cap 540 over the rocker arm support 223 such that the groove 541 covers the cylindrical base 531 and the circular or semicircular projection 543 is positioned within the cylindrical or semi-circular hole 226. The rocker cap 540 may be fastened to the rocker arm support 223 by screwing a thread-forming screw 544 through the non-threaded hole 542 formed in the rocker cap 540 and into the non-threaded hole 225 formed in the rocker arm support 223, as shown in FIGS. 34 to 36. In this configuration, the cylindrical base 531 can rotate within the cylindrical hole formed by semi-cylindrical grooves 224 and 541.

The armature 550 may be configured so that it can be rotatably coupled at a first location (preferably at or near its second end) to the crank 525 and at a second location (preferably at an intermediate location between its first and second ends) to the rocker arm 530. Optionally, the armature 550 may also be configured so that it can be rotatably coupled at a third location (preferably at the same distance along the length of the armature as the second location) to the rocker arm 530. The armature 550 may comprise an armature body 551 having a first end and a second end, and a first arm 560 having a first end and a second end. The armature 550 may also comprise a second arm 561 having a first end and a second end. The first ends of the first and second arms 560 and 561 are preferably coupled to the second end of the armature body 551. The first end of the armature body 551 defines the first end of the armature 550, and the second end of the first arm 560 defines the second end of the armature 550.

The armature body 551, shown in FIGS. 36*a* to 40, may have a concave top surface 552, first and second convex side surfaces 553 and 554, a flat bottom surface 555, a rounded tip 556, and a flat back surface 557. The rounded tip 556 defines the first end of the armature body 551 (and the first end of the armature 550), and the flat back surface 557 defines the second end of the armature body 551. First and second concave grooves 558 and 559 may be formed in the first and second side surfaces 553 and 554, respectively.

The first arm 560 may extend backward from the back surface 557 of the armature body 551 near its point of intersection with the first side surface 553, and a second arm 561 may extend backward from the back surface 557 of the armature body 551 near its point of intersection with the second side surface 554. The first arm 560 may be longer than the second arm 561. Preferably, both arms 560 and 561 extend in a parallel direction that is orthogonal to the back surface 557 of the armature body 551. Gussets 562 and 563 may be formed along the first and second arms 560 and 561 and the back surface 557 of the body 501 to increase the strength of the joints.

Figure 38:
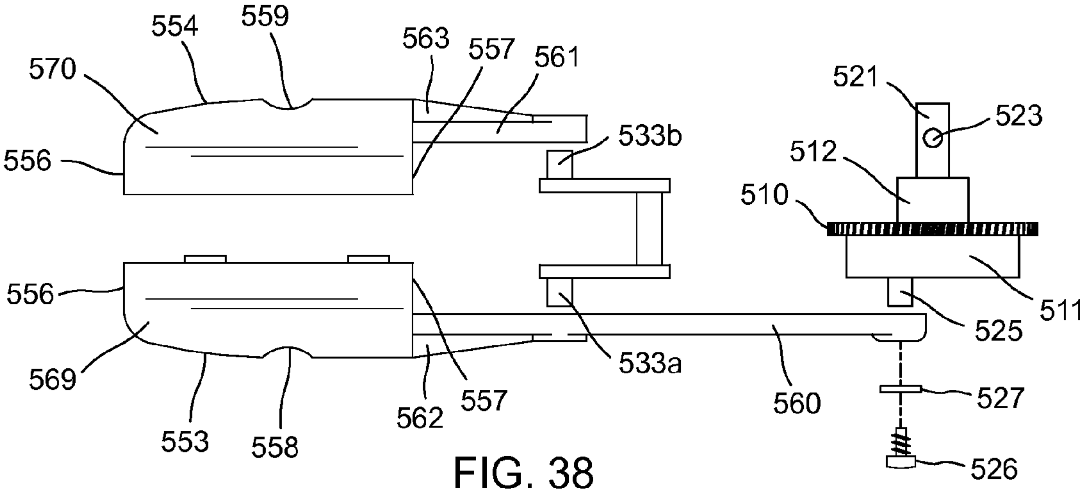
FIG. 38 is a top view of a first armature portion, a second armature portion, a rocker arm, a crank, a worm gear, and an axle in accordance with one embodiment of the present invention.
Figure 39:
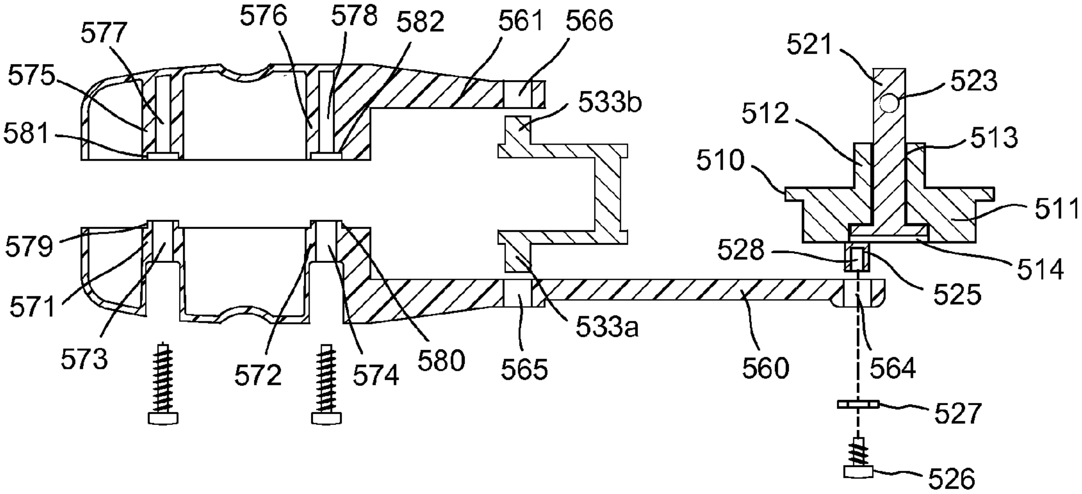
FIG. 39 is a cross-sectional view through a horizontal plane of a first armature portion, a second armature portion, a rocker arm, a crank, a worm gear, and an axle in accordance with one embodiment of the present invention.
Figure 40:
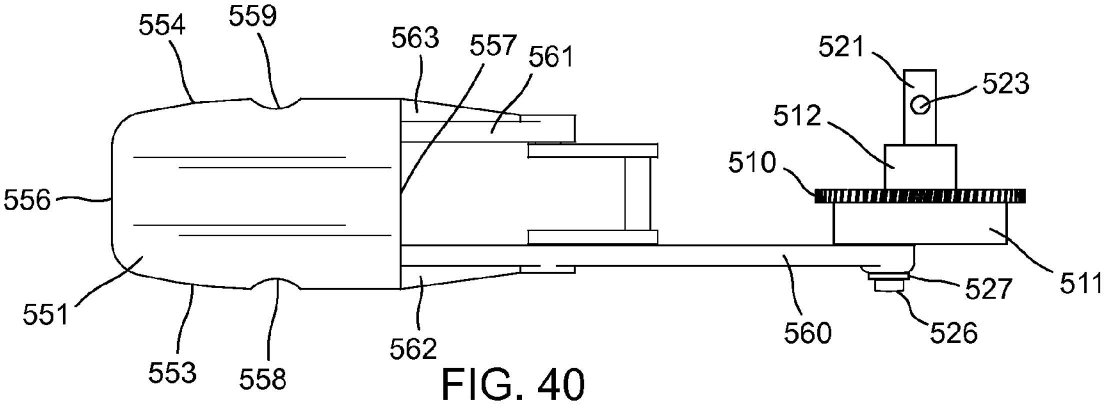
FIG. 40 is a top view of an armature, a rocker arm, a worm gear, and an axle in accordance with one embodiment of the present invention.

A first hole 564 may be formed in the first arm 560, preferably at or near its second end; a second hole 565 may be formed in the first arm 560 between its first end and the first hole 564; and, a third hole 566 may be formed in the second arm 561, preferably at or near its second end. The third hole 566 is preferably coaxial with the second hole 565. The first hole 564 may provide the means for rotatably coupling the armature 550 at a first location to the crank 525, and the second and third holes 565 and 566 may provide the means for rotatably coupling the armature 550 at second and third locations, respectively, to the rocker arm 530. The armature 550 may be rotatably coupled to the crank 525 by positioning the crank 525 within the first hole 564, and may be rotatably coupled to the rocker arm 530 by positioning the first and second projections 533*a* and 533*b* within the second and third holes 565 and 566, as shown in FIGS. 38 to 40. A thread-forming screw 526 may be inserted through a washer 527 and screwed into a non-threaded hole 528 formed in the crank 525, thereby securing the crank 525 within the first hole 564.

The armature 550 may be formed of first and second armature portions 567 and 568, as shown in FIGS. 36*a* to 39. The first armature portion 567 may comprise a first armature body portion 569 and the first arm 560, and the second armature portion 568 may comprise a second armature body portion 570 and the second arm 561. First and second armature columns 571 and 572 having first and second non-threaded holes 573 and 574 formed through their axes may be formed in the first armature body portion 569, and third and fourth armature columns 575 and 576 having third and fourth non-threaded holes 577 and 578 formed through their axes may be formed in the second armature body portion 570. Projections 579 and 580 formed in the side surface of the first armature body portion 569 may be configured to mate with recesses 581 and 582 formed on the side surface of the second armature body portion 570, thereby facilitating alignment of the first and second armature body portions 569 and 570. The first and second armature portions 567 and 568 may be coupled to one another by screwing a first thread-forming screw 581 through the first hole 573 and into the third hole 577, and by screwing a second thread-forming screw 582 through the second hole 574 and into the fourth hole 578.

Figure 41:
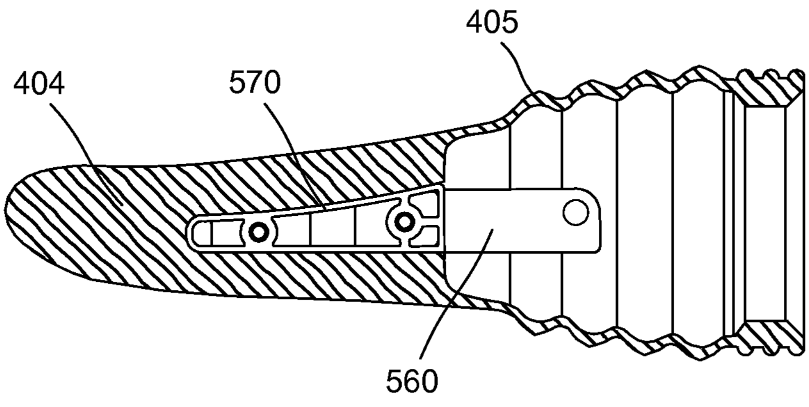
FIG. 41 is a cross-sectional view through a vertical plane showing an armature coupled to a massage head in accordance with one embodiment of the present invention.
Figure 42:
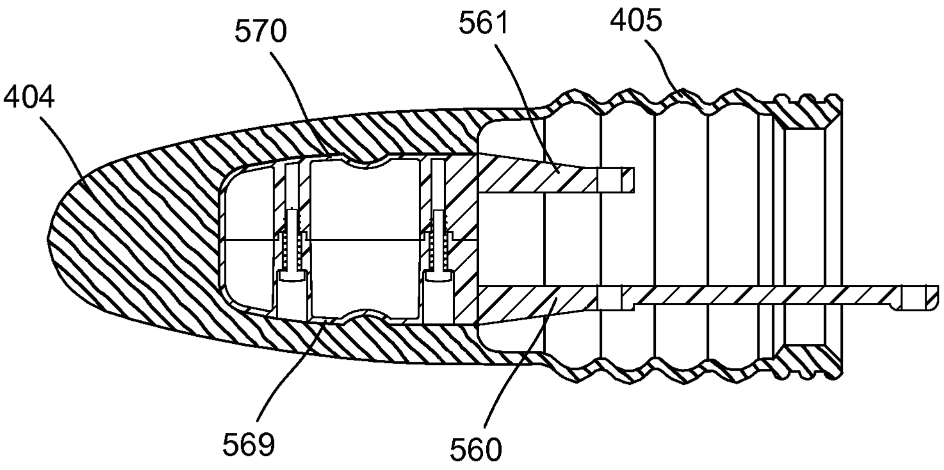
FIG. 42 is a cross-sectional view through a horizontal plane showing an armature coupled to a massage head in accordance with one embodiment of the present invention.
Figure 43:
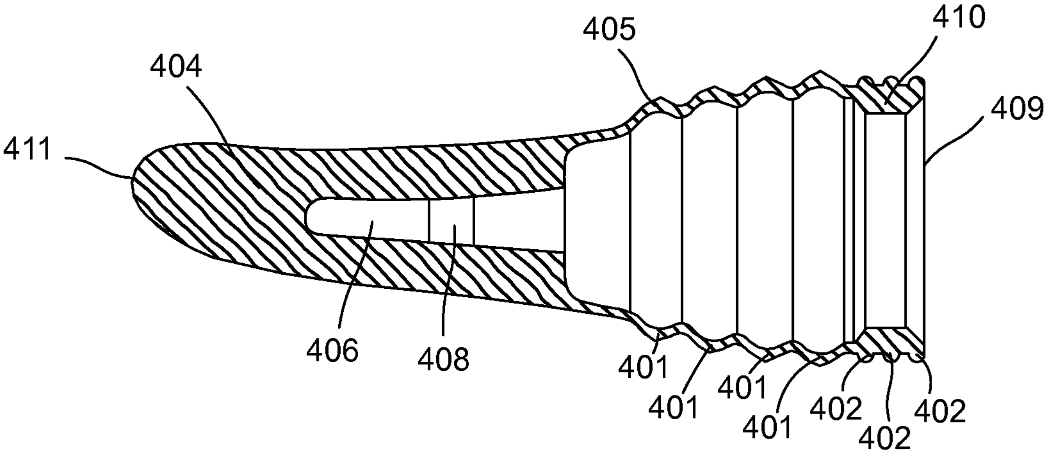
FIG. 43 is a cross-sectional view through a vertical plane showing a massage head in accordance with one embodiment of the present invention.
Figure 44:
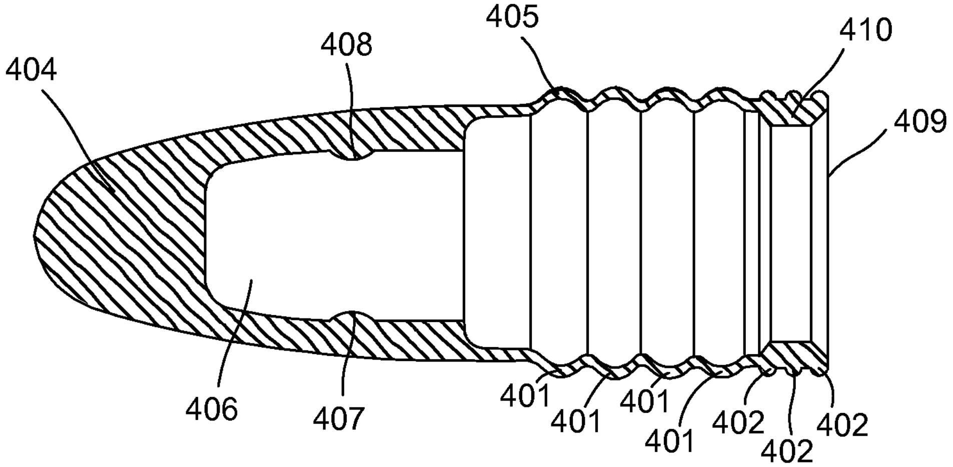
FIG. 44 is a cross-sectional view through a horizontal plane showing a massage head in accordance with one embodiment of the present invention.

The armature 550 may be configured for coupling to the massage head 400, as shown in FIGS. 41 and 42. One embodiment of the massage head 400 is shown in FIGS. 43 and 44. The massage head 400 may comprise a massage head body 404 and a tubular wall 405 extending backward therefrom. The massage head body 404 may have a cavity 406 formed therein. The cavity 406 may be approximately the same shape and size as the outer surface of the armature body 551, so that the armature body 551 can be tightly housed within the cavity 406. Convex projections 407 and 408 may be formed on the massage head body 404 so as to extend inward from opposite sides of the cavity 406. The projections 407 and 408 may be configured to be received into the first and second concave grooves 558 and 559 formed on the side surfaces 553 and 554 of the armature body 551, helping to prevent unintentional decoupling of the armature 550 from the massage head 400.

Figure 45:
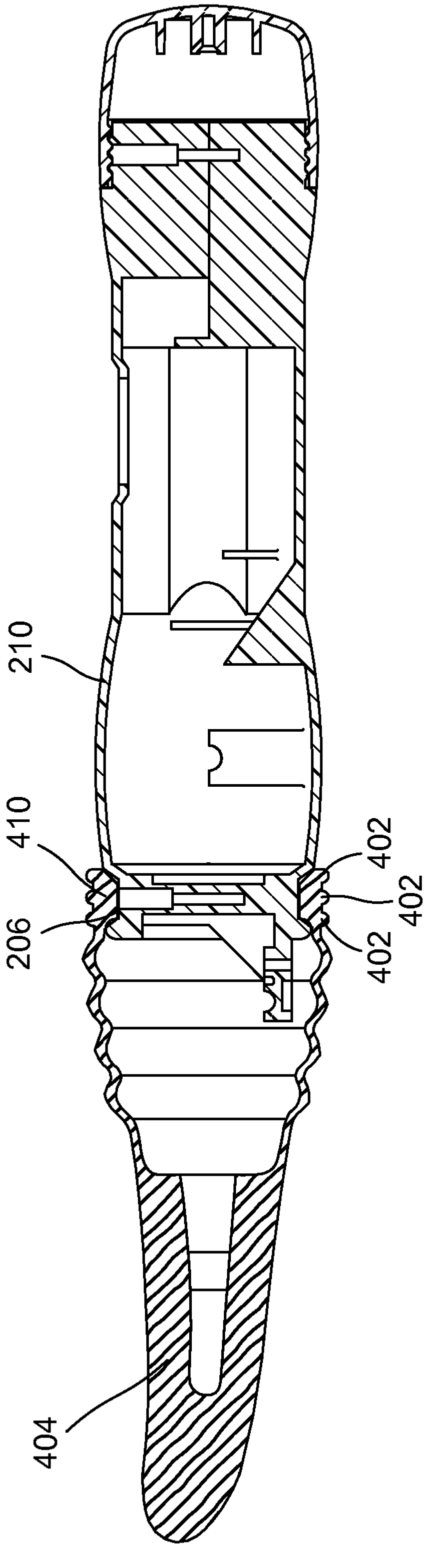
FIG. 45 is a cross-sectional view through a vertical plane showing a massage head coupled to a housing in accordance with one embodiment of the present invention.
Figure 46:
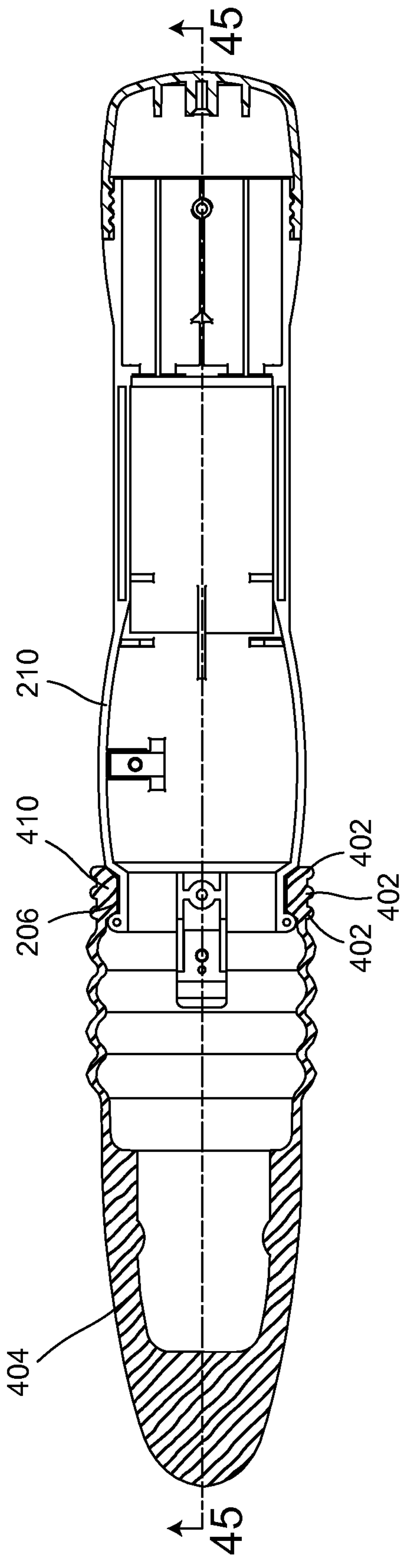
FIG. 46 is a partial cross-sectional view through a horizontal plane showing a massage head coupled to a housing in accordance with one embodiment of the present invention.

The tubular wall 405 of the massage head 400 may be configured for detachable coupling to the front end of the housing 200, as shown in FIGS. 45 and 46. The back end of the tubular wall 405 may be defined by a circular opening 409 that is designed to stretched radially outward so as to fit over the front circular opening 211 at the front end of the housing 200. An internal flange 410 may be formed at or near the circular opening 409 and configured to be received into the groove 206 formed at the front end of the housing 200 when the tubular wall 405 is stretched over the front end of the housing 200. In this manner, the massage head 400 can be detachably coupled to the housing 200. One or more ridges 402 may be formed around the outer surface of the massage head 400, preferably opposite the internal flange 410. The ridges 402 increase the radial stiffness of the tubular wall 402, thereby further securing the internal flange 410 within the groove 206 so as to prevent the massage head 400 from unintentionally decoupling from the housing 200.

One or more corrugations 401 may be formed in the tubular wall 405 between the ridges 402 and the massage head body 404. The corrugations 401 increase flexibility in the tubular wall 405, allowing the massage head body 404 to move relative to the housing 200 with greater ease and range of motion. Other embodiments may use different configurations to provide flexibility in the tubular wall. For example, in certain embodiments, the tubular wall 405 may have a bulbous design (not shown) that provides the necessary flexibility and range of motion. In some embodiments, the tubular wall 405 may be omitted entirely, in which case the massage head 400 may be coupled to the armature 550 but not to the housing 200.

The massage head body 404 may have a shape that simulates a human tongue, tapering forward to a rounded and slightly upturned tip 411 that defines the first end of the massage head 400. A shallow groove 403, shown in FIG. 2, may be formed lengthwise along the centerline of the top surface of the massage body 404, simulating the structure of the median sulcus in a human tongue. Furthermore, at least a portion of the outer surface of the massage head 400, preferably including outer surface of the massage head body 404 and its tip 411, may be textured so as to simulate the papillae on a human tongue. Furthermore, the massage head 400 may be formed of a material, such as silicone rubber, that simulates the suppleness of a human tongue.

Figure 49:
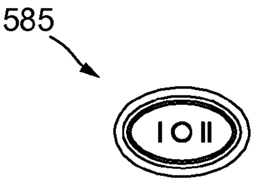
Figure 50:
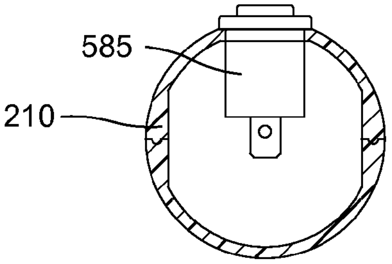
FIG. 50 is a cross-sectional view showing a switch mounted to a housing in accordance with one embodiment of the present invention.
Figure 51:
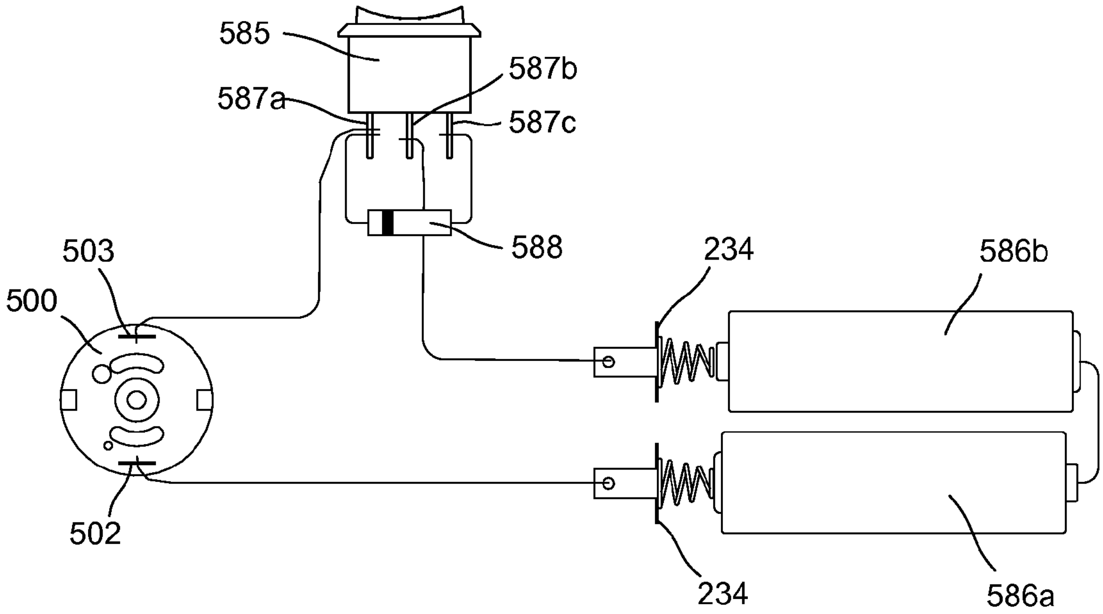
FIG. 51 is a schematic illustration of electrical connections between a switch, a motor, and a pair of batteries in accordance with one embodiment of the present invention.
Figure 52A:
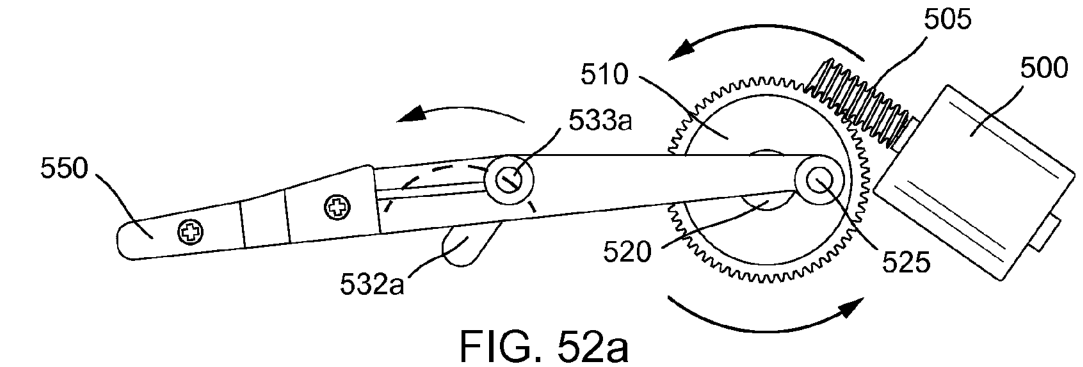
FIGS. 52*a* to 52*d* are side views of a drive mechanism at different stages of operation in accordance with one embodiment of the present invention.
Figure 52B:
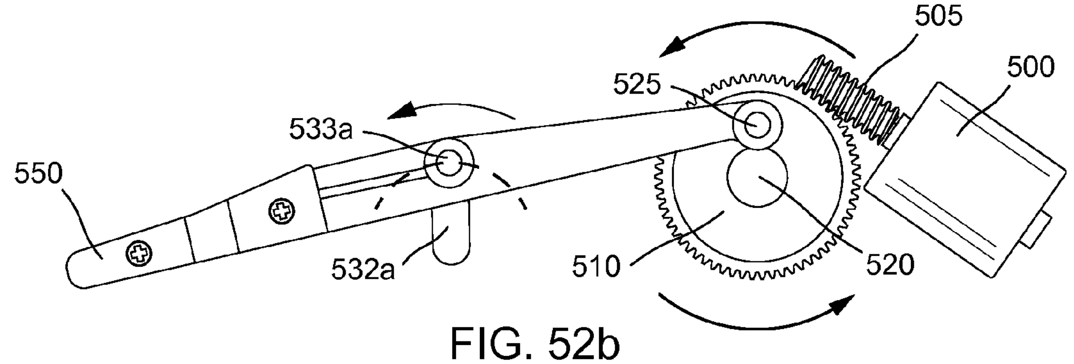
Figure 52C:
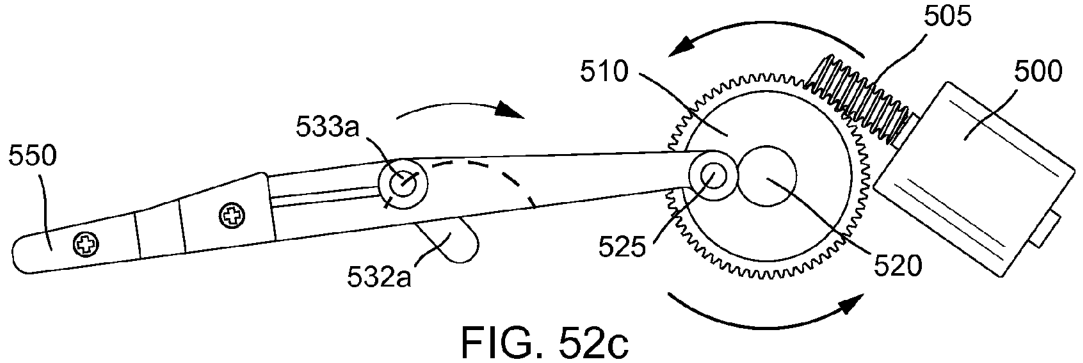
Figure 52D:
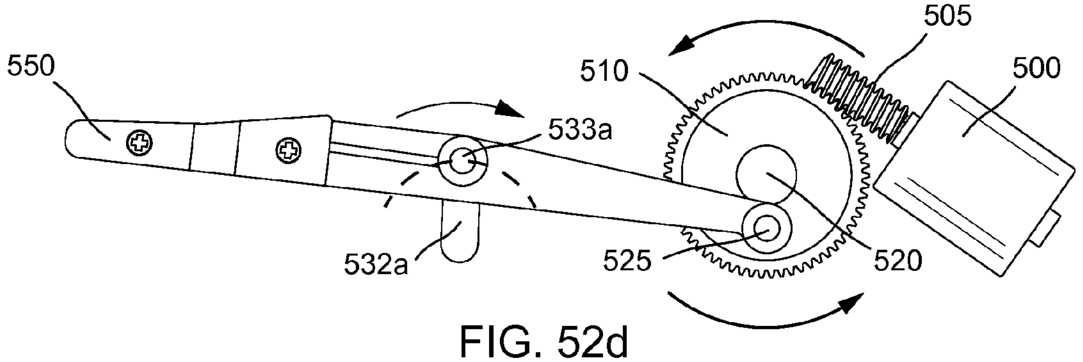

The switch 585 may be mounted by conventional means within the hole 209 formed in the housing 200 between the first and second cylindrical protrusions 202 and 203 (shown in FIGS. 3 to 5), as shown in FIG. 50. Preferably, the switch 585 is a three-way rocker switch, of the type shown in FIGS. 47 to 49. The switch 585 may control operation of the drive mechanism by completing or breaking electrical communication between the power supply, such as batteries **586*a* and 586*b*, and the motor 500. In the preferred configuration, shown in FIG. 51, the batteries 586*a* and 586*b* are connected in series, via the spring contacts 234 and the contact disc 310, to a second terminal 587*b* of the switch 585, and to a negative terminal 502 of the motor 500. The positive terminal 503 of the motor 500 is connected to a first terminal 587*a* of the switch 585. The first and third terminals 587*a* and 587*c* of the switch 585 are connected to each other through a diode 588. When the switch 585 is in a first "on" position, the electrical circuit between the batteries 586*a* and 586*b*, and the motor 500, is closed, bypassing the diode 588 and thereby allowing the motor 500 to operate at higher speed. When the switch 585 is in a second "on" position, the electrical circuit between the batteries 586*a* and 586*b*, and the motor 500, is closed, but the current passes through the forward-biased diode 588, resulting in a voltage drop across the diode 588 and causing a decrease in current through the motor 500. Accordingly, when the switch is set to the second "on" position, the motor 500 operates at a lower speed. When the switch 585 is in the "off" position, the circuit between the batteries 586*a* and 586*b* and the motor 500, is open, and therefore the motor 500** does not operate.

Figure 53:
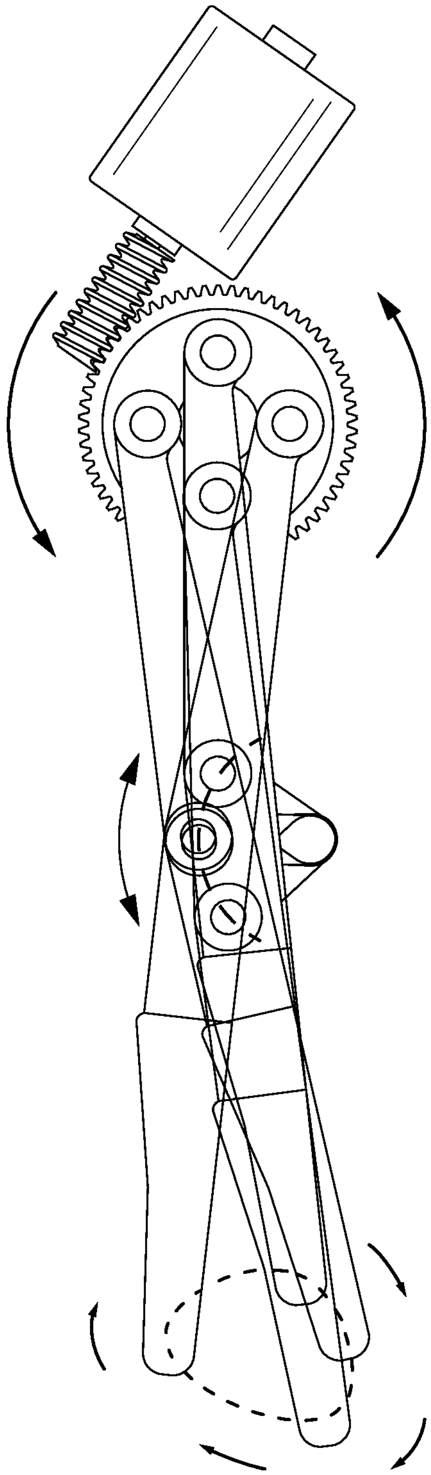
FIG. 53 is a side view showing a drive mechanism at different stages of operation, with the armature and crank at the different stages superimposed over each other, in accordance with one embodiment of the present invention.

In operation, when the switch 585 is switched to either "on" position, the motor shaft 501 rotates, causing the worm 505 and worm gear 510 to rotate. Rotation of the worm gear 510 causes the crank 525 to move in a circular path around the axle 520, as shown in FIGS. **52*a* to 52*d* and 53. FIGS. 52*a* to 52*d* show a drive mechanism at four different stages as the crank 525 moves in its circular path, and FIG. 53 shows those four different stages of the drive mechanism superimposed over one another in a single drawing. The circular path of the crank 525 defines a plane that is orthogonal to the axis of the axle 520 and is parallel to the axis of the housing 200. The circular motion of the crank 525 is translated to the armature 550 at the location of their coupling (preferably at or near the second end of the armature 550), thereby creating motion in the armature 550 that causes the rocker arm 530 to pivot around the location of its coupling with the housing 200 (preferably at or near the first end of the rocker arm 530), and to oscillate back and forth along an arc at the location of its coupling with the armature 550 (preferably at or near the second end of the rocker arm 530), as shown by dashed lines in FIGS. 52*a* to 52*d* and 53. The armature 550 is constrained, at the location of its coupling with the rocker arm 530, to oscillate along the path of this arc. The circular motion of the armature 550 at the location where it couples to the crank 525, combined with the oscillating motion of the armature 550 at the location where it couples to the rocker arm 530, causes the first end of the armature 550 to move in a closed plane path, as shown by a dashed line in FIG. 53. The plane defined by the closed plane motion of the armature 550 is parallel to the plane defined by the circular motion of the crank 525. As the crank 525 moves in its circular path in the counter-clockwise direction shown, the tip of the first armature moves forward and slightly downward, then moves sharply upward and slightly backward, and finally moves downward and backward to its starting position. This motion of the first end of the armature 550** imitates the thrusting and flicking movement of a human tongue when licking an object.

The closed plane movement in the first end of the armature 550 is mirrored by the massage head body 404 to which it is attached. The tubular wall 405 of the massage head 400 deforms during operation so as to allow the massage head body 404 to follow this closed plane path. The movement of the massage head body 404 creates a massage effect for the user that realistically simulates stimulation by a human tongue. This massage effect may be enhanced by the life-like materials used to make the massage head 400, by the tongue-shaped structure of the massage head body 404, and by the textured surface of the massage head 400, which simulates the natural surface of a human tongue.

Figure 54:
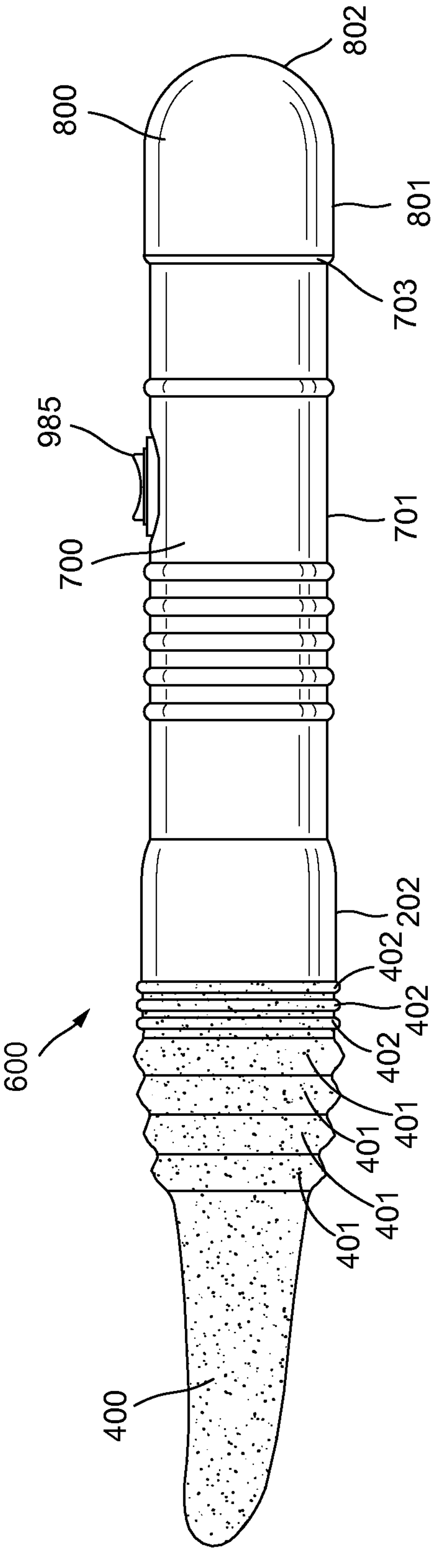
FIG. 54 is a side view of a personal massager in accordance with another embodiment of the present invention.
Figure 55:
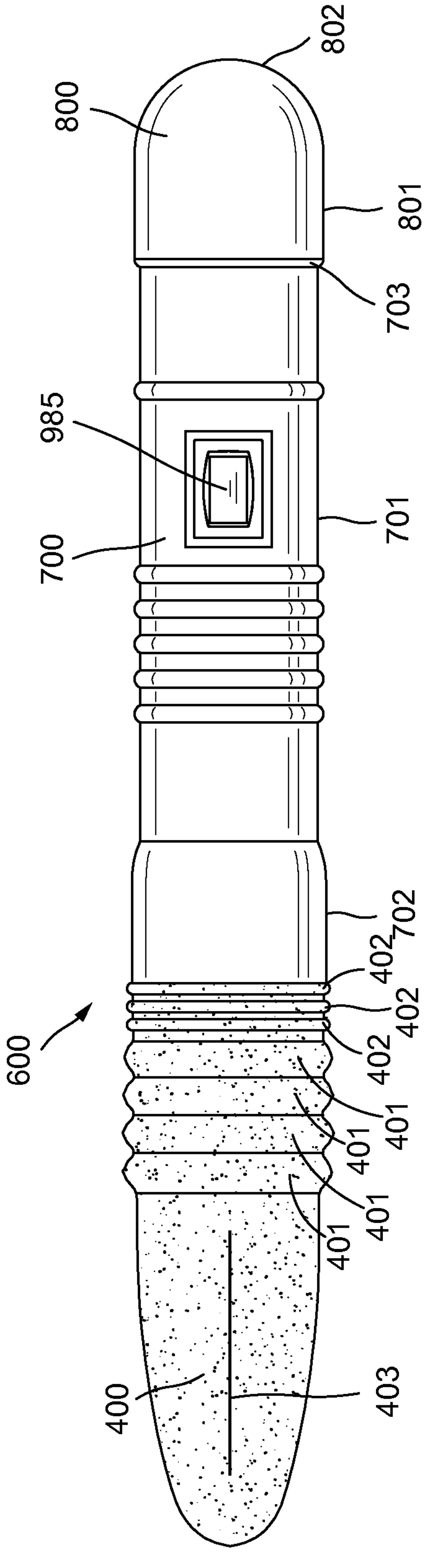
FIG. 55 is a top view of the personal massager of FIG. 54.
Figure 56:
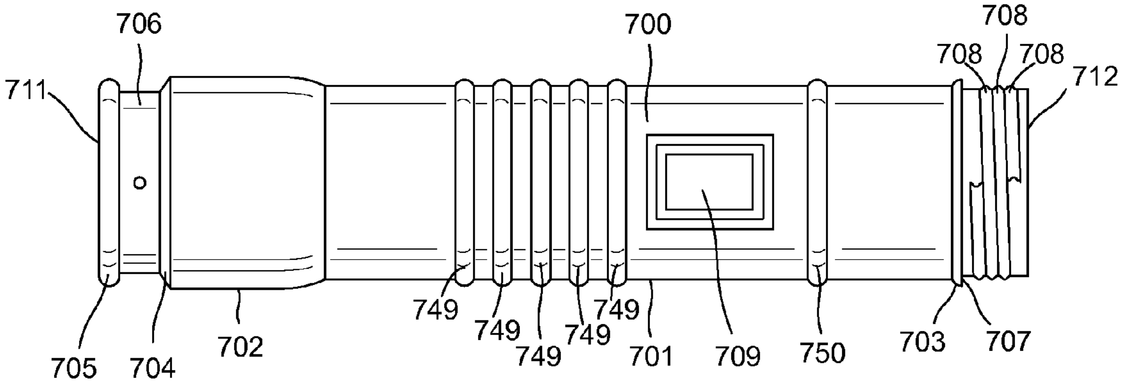
FIG. 56 is a top view showing the exterior of a housing in accordance with another embodiment of the present invention.
Figure 57:
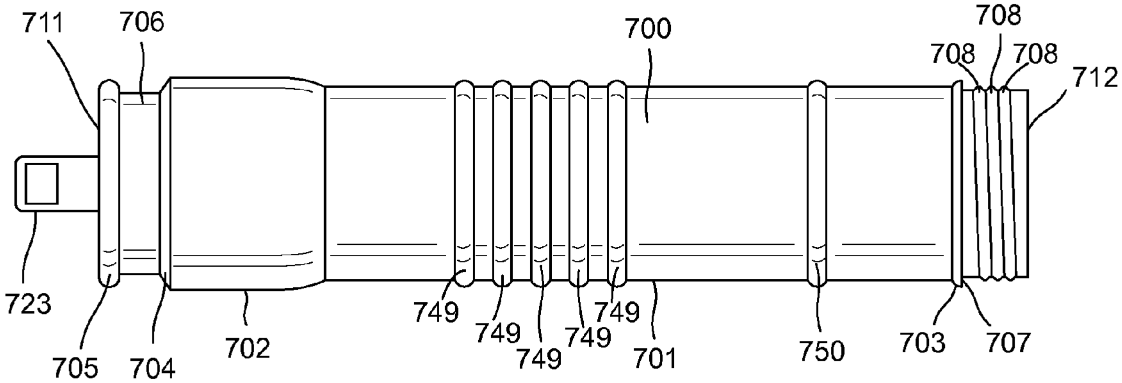
FIG. 57 is a bottom view showing the exterior of the housing of FIG. 56.
Figure 58:
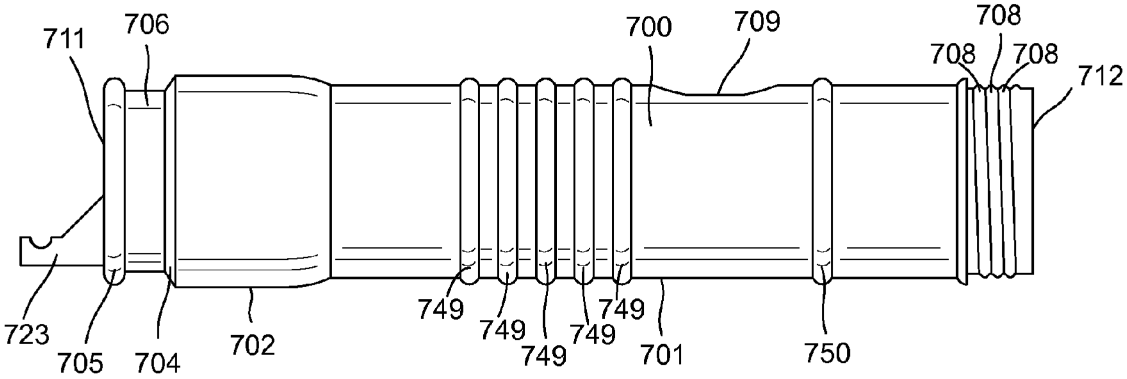
FIG. 58 is a side view showing the exterior of the housing of FIG. 56.
Figure 59:
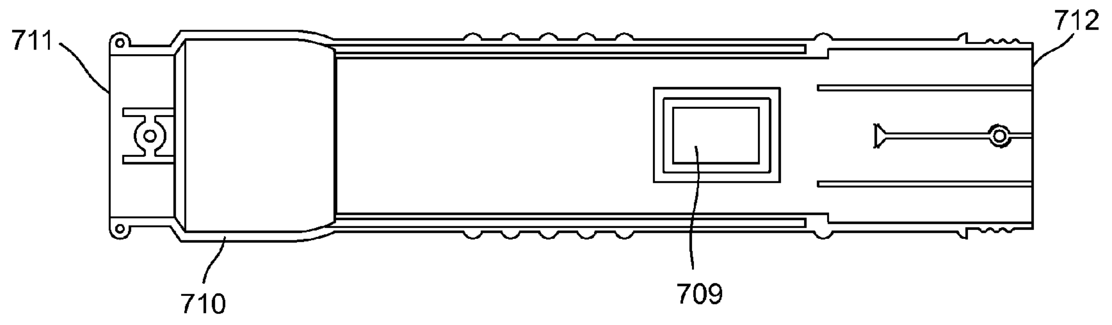
FIG. 59 is a cross-sectional through a horizontal plane showing the upper portion of the interior of the housing of FIG. 56.
Figure 60:
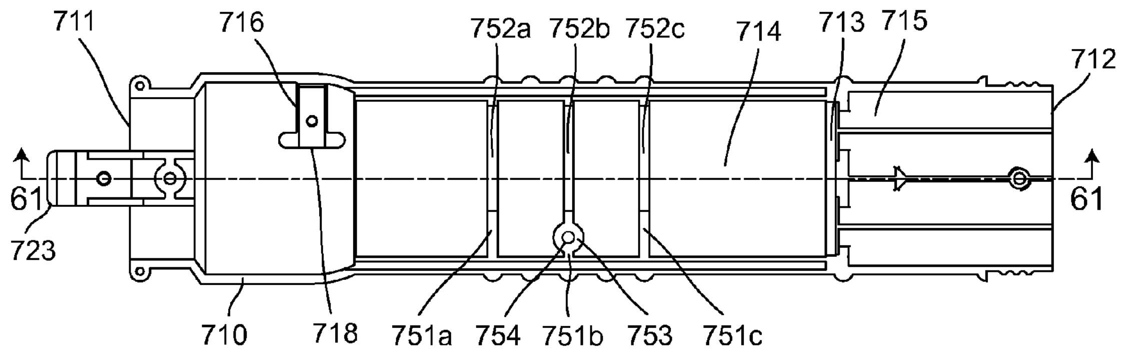
FIG. 60 is a cross-sectional view through a horizontal plane showing the lower portion of the interior of the housing of FIG. 56.
Figure 61:
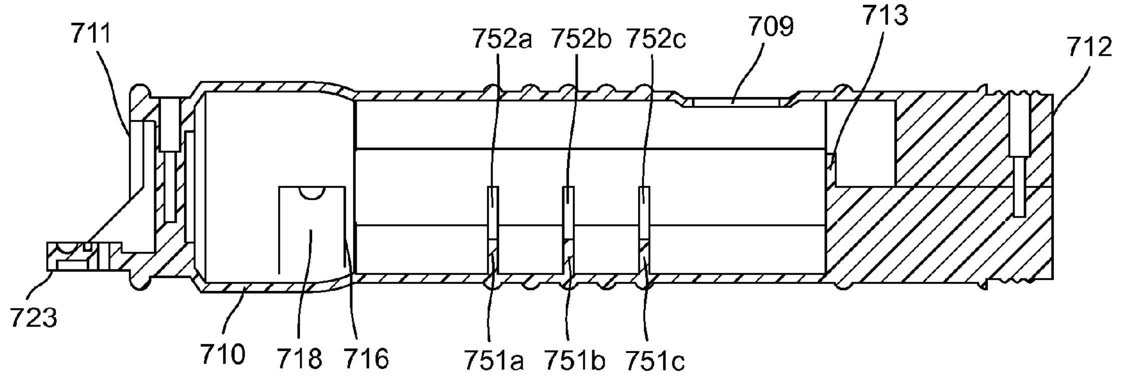
FIG. 61 is a cross-sectional view through a vertical plane showing the interior of the housing of FIG. 56.
Figure 62:
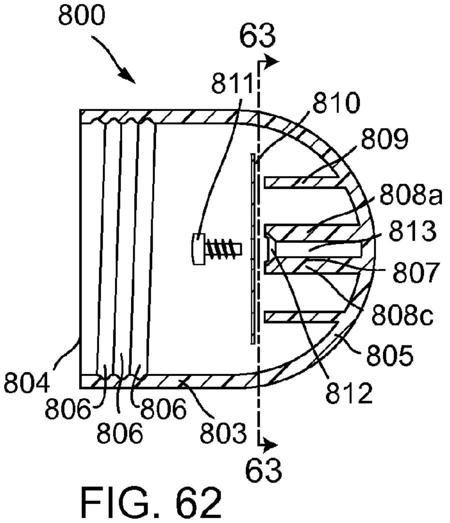
FIGS. 62 to 64 are cross-sectional views through a vertical plane showing a battery cap in accordance with another embodiment of the present invention.
Figure 63:
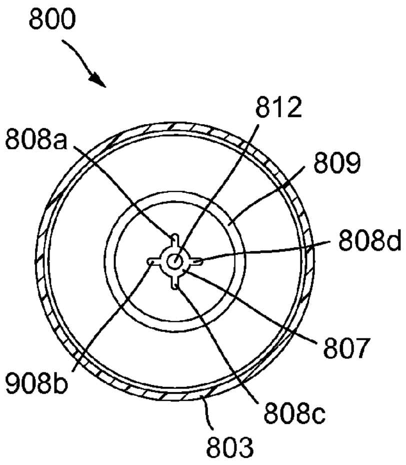
Figure 64:
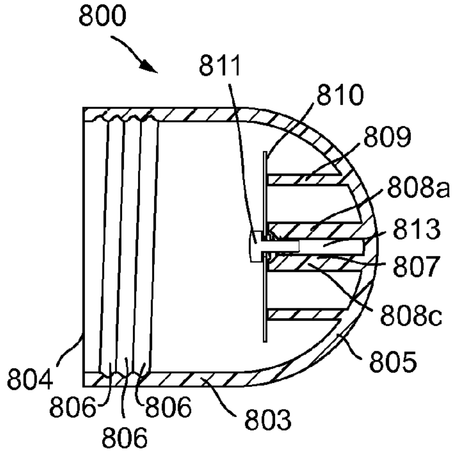

Another embodiment of the personal massager 600, wherein the housing 700 is suitable for a configuration in which the gear drive comprises a pair of bevel gears and the motor is a gear motor, is shown in FIGS. 54 to 55. The personal massager 600, similarly to the personal massager 100, may comprise a housing 700, a battery cap 900, and a massage head 400. The exterior of the housing 700 of this embodiment is shown in FIGS. 56 to 58, and the interior is shown in FIGS. 59 to 61. Referring to FIGS. 56 to 58, the exterior of the housing 700 is similar in a number of respects to the housing 200 of FIGS. 3 to 5, but incorporates several modifications. The first cylindrical protrusion 702 may have a straighter outer side surface than the first cylindrical protrusion 202, which may be convex along its entire length. A series of ridges 749 and 750, absent on the housing 200, may be formed around the cylindrical outer side surface 701 the housing 700. A ridge 703 that is truncated by a second annular wall 707 may be formed towards the back end of the housing 700, replacing the second cylindrical protrusion 203 of the housing 200. A square hole 709 may be formed through the top surface of the housing 200, rather than the oval hole 209 of the housing 200. Furthermore, the housing 700 may be longer than the housing 200. This greater length may be necessary to accommodate the gear drive, which is typically longer than a standard DC motor because of the internal gears that perform gear reduction. In other aspects, the exterior of the housing 700 of FIGS. 56 to 58 is similar to that of the housing 200 of FIGS. 3 to 5.

Referring to FIGS. 59 to 61, vertical motor supports 751*a*, 751*b*, and 751*c* may be transversely formed on, or attached to, the inner surface of the housing 700. Semi-cylindrical grooves 752*a*, 752*b*, and 752*c* may be formed through horizontal top edges of the supports 751*a*, 751*b*, and 751*c*. Preferably, the grooves 752*a*, 752*b*, and 752*c* have approximately the same diameter as the motor, and their axes form a line that is parallel to, and laterally offset from, the axis of the housing 700. A vertical column 753, which is preferably cylindrical, may be formed through at least one of the supports, preferably the middle support 751*b*, thereby bisecting the support 751*b*. A non-threaded hole 754 may be formed vertically through the axis of the column 753. Other features of the interior of the housing 700 of FIGS. 59 to 61 are similar to those of the housing 200 shown in FIGS. 6 to 8.

Figure 65:
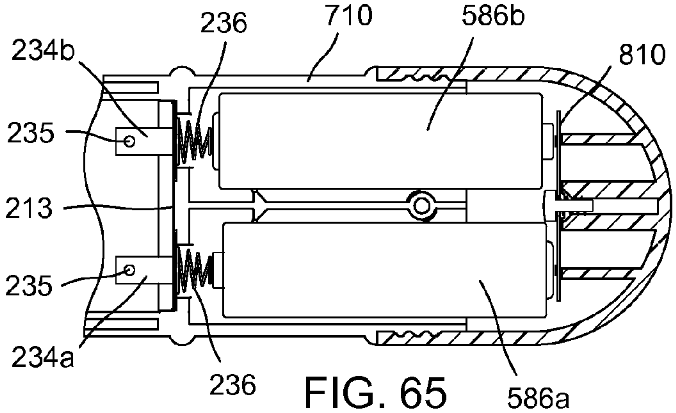
FIG. 65 is a partial cross-sectional view through a horizontal plane showing a housing, a battery cap, and a pair of batteries in accordance with another embodiment of the present invention.

A battery cap 800 suitable for use with the personal massager 600 is shown in FIGS. 62 to 65. The cylindrical wall 803 of the battery cap 800 shown in FIGS. 62 to 64 has straight side surfaces, whereas the cylindrical wall 303 of the battery cap 300 shown in FIGS. 15 to 17 has slightly convex side surfaces. Additionally, the rear wall 805 of the battery cap 800 is semi-circular, as opposed to the slightly convex rear wall 305 of the battery cap 300. Accordingly, the column 807, gussets 808*a*, 808*b*, 808*c*, and 808*d*, and cylindrical disc support 809 of the battery cap 800 are longer than their corresponding structures in the battery cap 300 of FIGS. 15 to 17. Other aspects of the design of the battery cap 800, including its method of attachment to the housing 700 as shown in FIG. 65, are similar to those of the battery cap 300.

Figure 69:
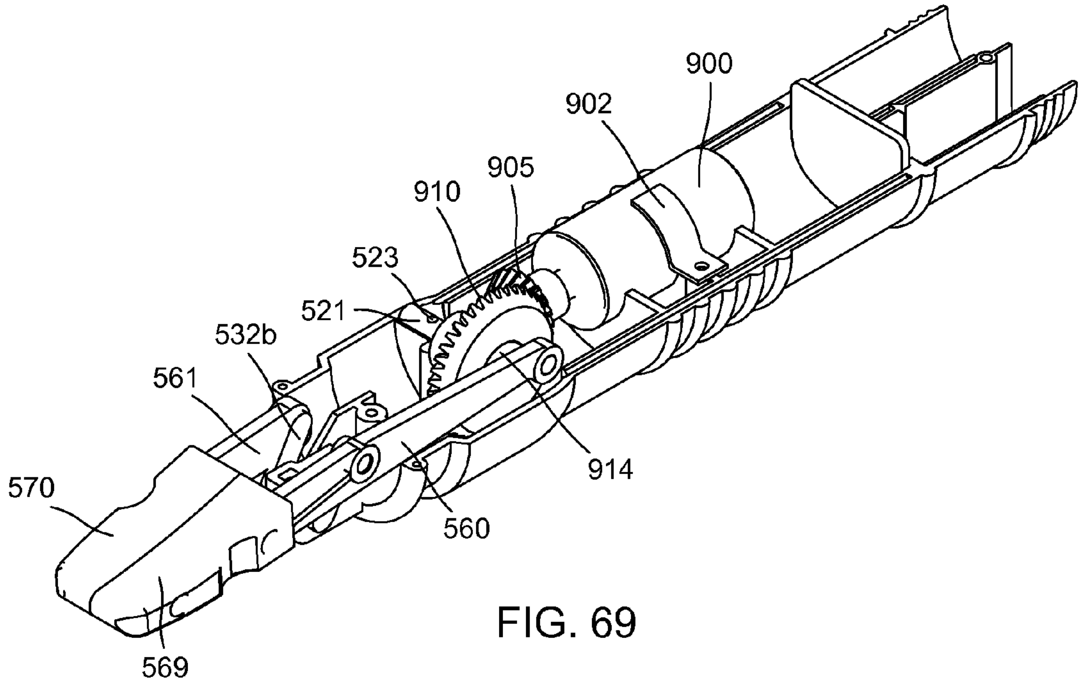
FIG. 69 is a perspective view showing a lower housing portion and a drive mechanism in accordance with another embodiment of the present invention.
Figure 70:
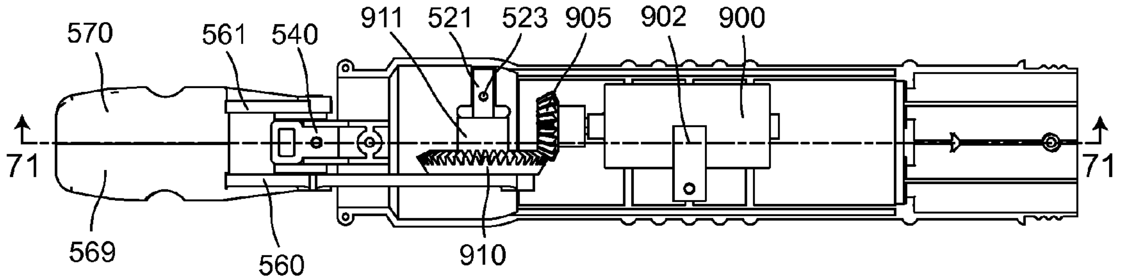
FIG. 70 is a top view showing a lower housing portion and a drive mechanism in accordance with another embodiment of the present invention.
Figure 71:
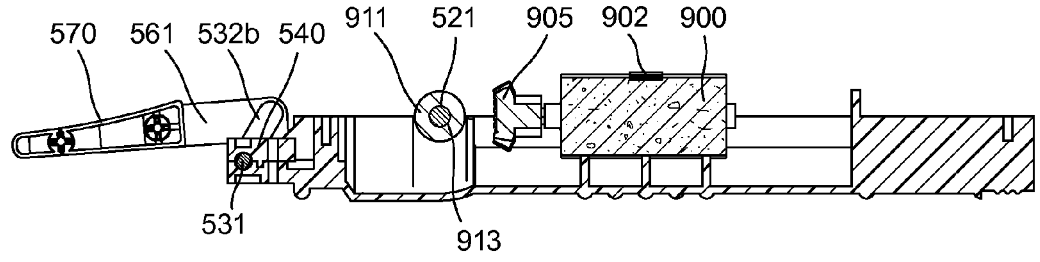
FIG. 71 is a cross-sectional view through a vertical plane showing a lower housing portion and a drive mechanism in accordance with another embodiment of the present invention.
Figure 72:
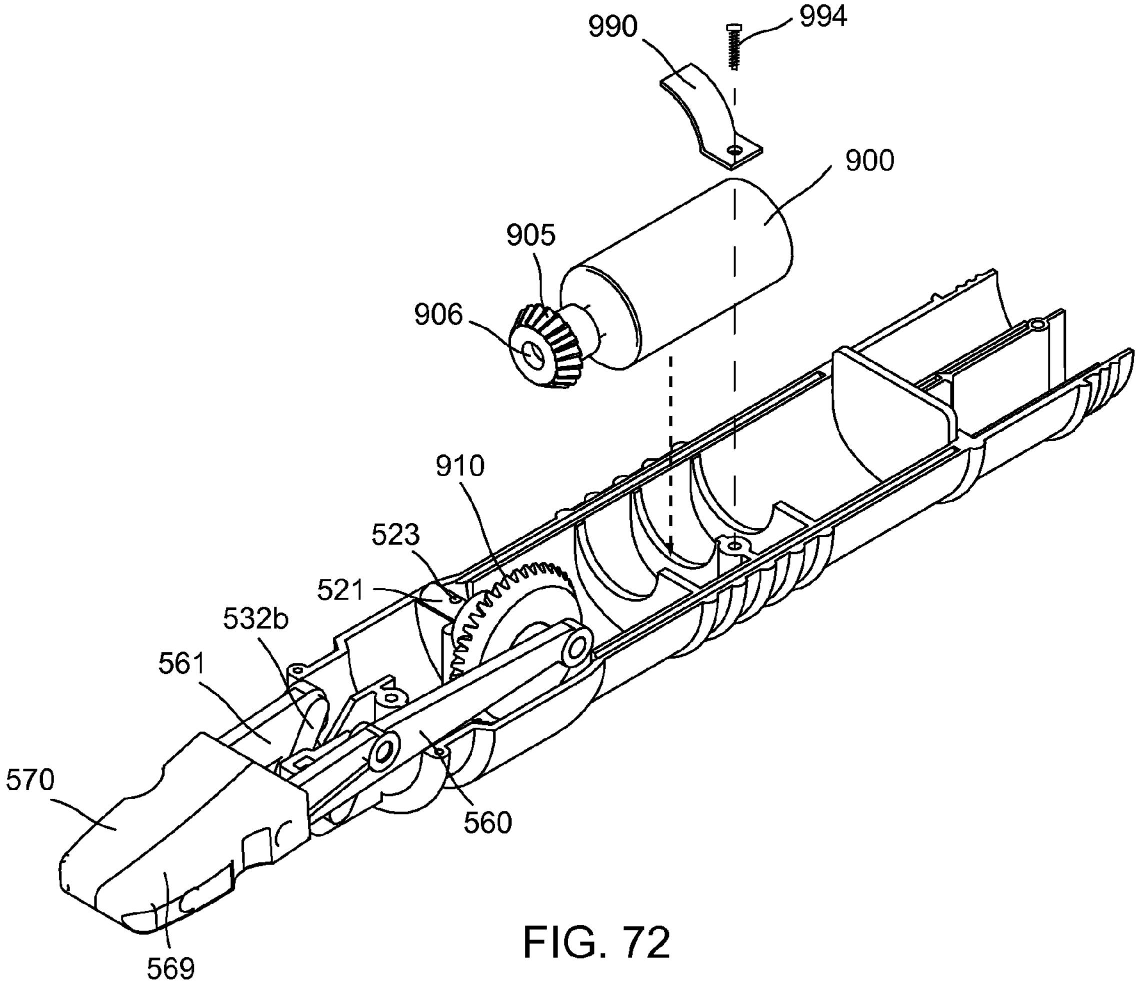
FIG. 72 is a perspective view showing the mounting of a motor within a lower housing portion in accordance with another embodiment of the present invention.
Figure 73:
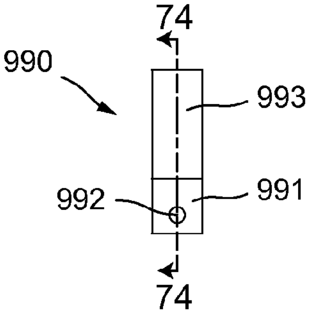
FIGS. 73 and 74 are top and side views showing a motor bracket in accordance with another embodiment of the present invention.
Figure 74:
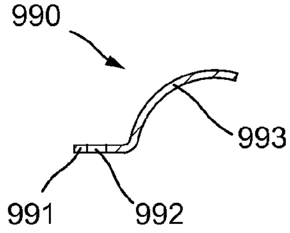
Figure 75:
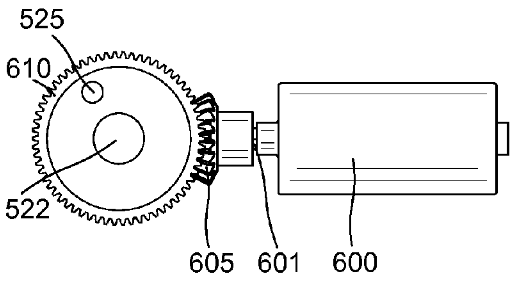
FIGS. 75 and 76 are side and top views of a drive mechanism in accordance with another embodiment of the present invention.
Figure 76:
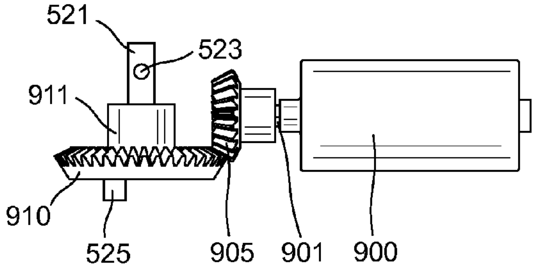

FIGS. 69 to 71 show a drive mechanism housed within the housing of FIGS. 56 to 61. The axle 520, crank 525, rocker arm 530, rocker cap 540, and armature 550 of this drive mechanism are the same as those employed in the drive mechanism shown in FIGS. 21 to 33. The motor 900 and gear drive (consisting of a bevel pinion gear 905 and a bevel gear 910) of the embodiment shown in FIGS. 69 to 71, however, are different from the corresponding structures in the embodiment shown in FIGS. 21 to 23. The motor 900 used with the personal massager 600 is preferably a gear motor, such as the SunTech model SU143G 3 Volt gear motor, as opposed to the standard DC motor 600 used with the personal massager 100. The motor 900 is preferably mounted horizontally within the semi-cylindrical grooves 752*a*, 752*b*, and 752*c* formed in the vertical motor supports 751*a*, 751*b*, and 751*c*, as shown in FIG. 61. The motor 900 may be secured to the housing 700 by a motor bracket 990, such as the bracket 990 shown in FIGS. 69, 72, 73, and 74. The motor bracket 990 may include a flat base 991 having a non-threaded hole 992 formed therethrough, and a curved bar 993 having a curvature that matches that of the outer surface of the motor 900. The motor bracket 990 may be placed over the motor 900 once it is positioned within the grooves 752*a*, 752*b*, and 752*c*, and a non-threaded screw 994 may be screwed through the hole 992 in the base 991 and into the non-threaded hole 754 in the column 753. Other techniques may be used to secure the motor 900 to the housing 700 instead of, or in addition to, using the motor bracket 990. For example, hot melt adhesive may be applied to at least one of the contact points between the motor 900 and the vertical motor supports 751*a*, 751*b*, and 751*c*.

The shaft 901 of the motor 900 may be inserted into the bore 906 of the bevel pinion gear 905, thereby coupling the pinion 905 to the shaft. The shaft 901 may have a key (not shown) that fits with a keyseat (not shown) in the bore 906, thereby preventing relative rotation between the shaft 901 and the pinion bevel gear 905. The motor 900 may be mounted in such a position that the teeth of the bevel pinion gear 905 mesh with the teeth of the bevel gear 910. While the number of teeth on the bevel pinion gear 905 and the bevel gear 910 may be selected to achieve a desired gear ratio and mechanical advantage, the majority of any desired gear reduction may be provided primarily from the gear drive within the gear motor 900. A cylindrical projection 911 may be formed on, or affixed to, the side of the bevel gear 910 facing the flat vertical surface 718 of the axle support 716. Preferably, the cylindrical projection 911 does not have teeth, and has an outer diameter that is smaller than that of the bevel gear 910. The length of the cylindrical projection 911 can be selected to ensure that the teeth of the bevel pinion gear 905 mesh with the teeth of the bevel gear 910.

Figure 77:
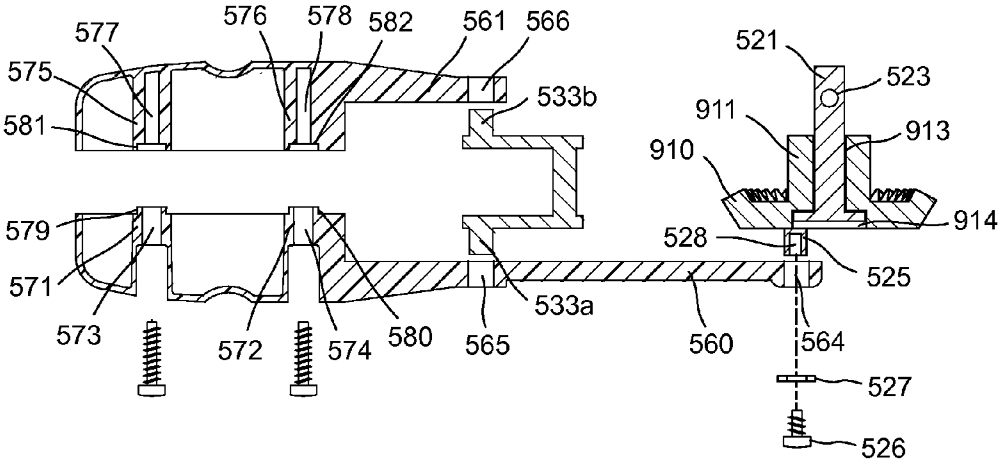
FIG. 77 is a cross-sectional view through a horizontal plane of a first armature portion, a second armature portion, a rocker arm, a crank, a worm gear, and an axle in accordance with another embodiment of the present invention.
Figure 78:
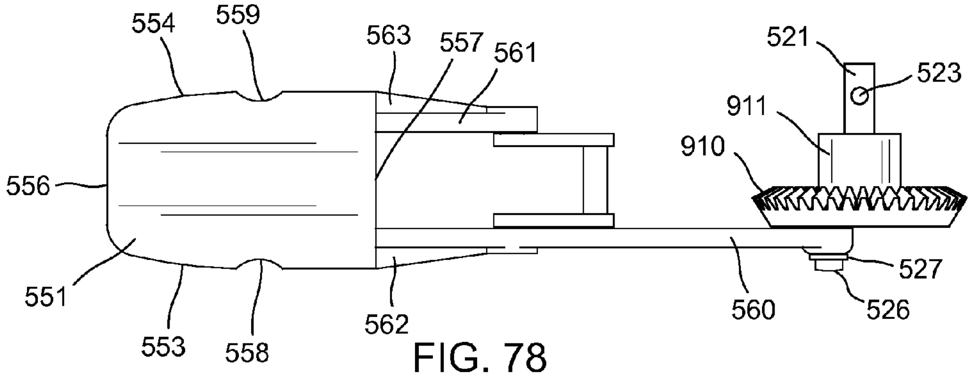
FIG. 78 is a top view of an armature, a rocker arm, a worm gear, and an axle in accordance with another embodiment of the present invention.

The bevel gear 910 may be mounted on the axle 520 by inserting the axle shaft 521 through the bore 913 (shown in FIGS. 71 and 77) of the bevel gear 910 and the cylindrical projection 911. Preferably, the joint between the axle 520 and the bevel gear 910 is not keyed, so that the bevel gear 910 can rotate relative to the axle 520. A cylindrical recess 914 (shown in FIGS. 69 and 77) may be formed around the bore 913 at the exposed side surface of the bevel gear 910 for receiving the head 522 of the axle 520. The axle 520 may be mounted on the axle support 716 in the same manner as described with respect to FIGS. 9 to 10. The crank 525 may be mounted eccentrically with respect to the axle 520 on the exposed side surface of the bevel gear 910. Referring to FIGS. 77 to 78, the armature 550 may be rotatably coupled to the crank 525 by positioning the crank 525 within the first hole 564, in the same manner as described with respect to FIGS. 38 to 40. The rocker arm 530 may be rotatably coupled to the rocker arm support 723 via the rocker cap 540 in the same manner as described with respect to FIGS. 34 to 35.

Figure 47:
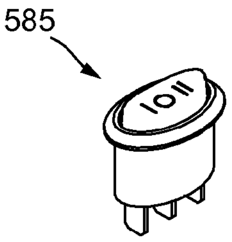
FIGS. 47 to 49 are perspective, side, and top views of a switch in accordance with one embodiment of the present invention.
Figure 48:
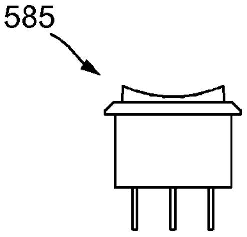
Figure 66:
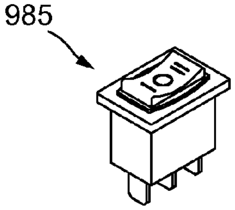
FIGS. 66 to 68 are perspective, side, and top views of a switch in accordance with another embodiment of the present invention.
Figure 67:
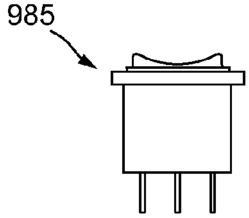
Figure 68:
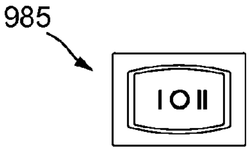

The switch 985 of FIGS. 66 to 68 is a three-way rocker switch that is similar in structure and operation to the switch 585 of FIGS. 47 to 49 except for having a square, rather than an oval, shape. The switch 985 may be mounted by conventional means within the hole 709 in the housing 700, and may control operation of the drive mechanism of the personal massager 600 in the same manner in which the switch 585 controls operation of the drive mechanism of the personal massager 100, as described with respect to FIG. 51. In operation, when the switch 985 is switched to either "on" position, the motor shaft 901 rotates, causing the bevel pinion gear 905 and bevel gear 910 to rotate, which causes the crank 525 to move in a circular path around the axle 520. The circular motion of the crank 525 creates the same motion in the armature 550 that is described with respect to FIGS. **52*a* to 52*d* and 53**.

Figure 79:
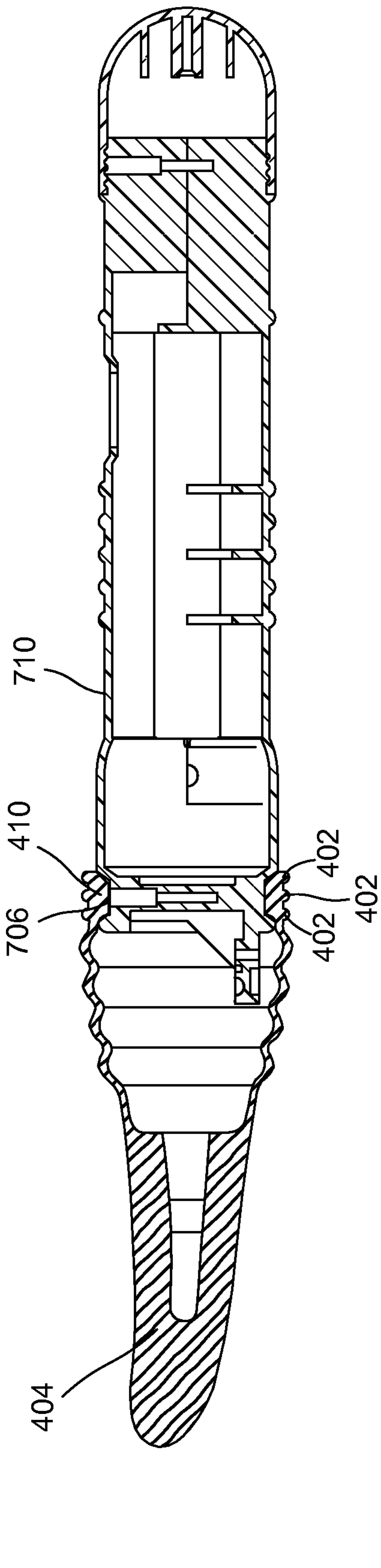
FIG. 79 is a cross-sectional view through a vertical plane showing a massage head coupled to a housing in accordance with another embodiment of the present invention.
Figure 80:
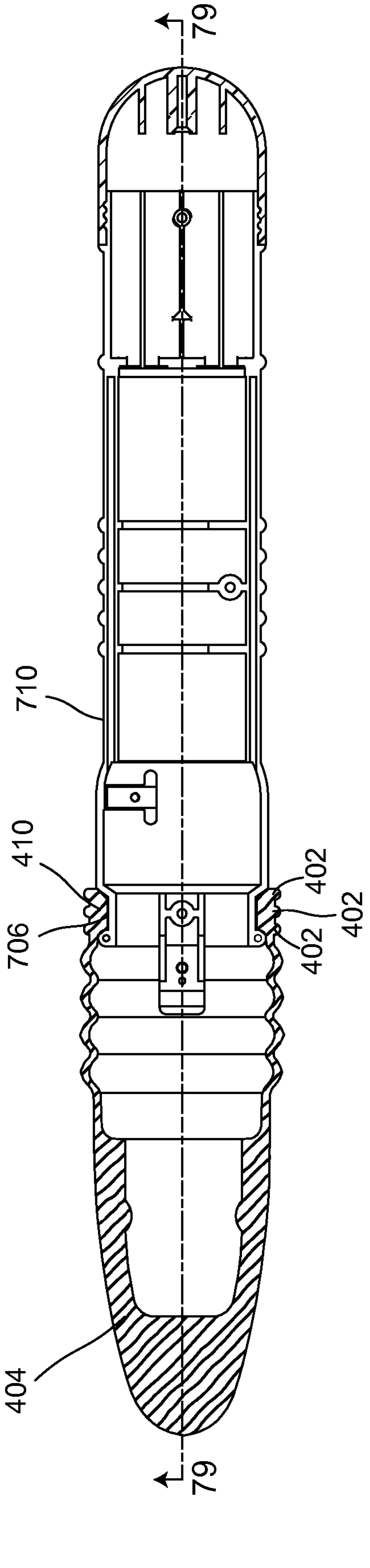
FIG. 80 is a partial cross-sectional view through a horizontal plane showing a massage head coupled to a housing in accordance with another embodiment of the present invention.

The tubular wall 405 of the massage head 400 may be detachably coupled to the front end of the housing 700 in the same manner in which it may be detachably coupled to the front end of the housing 200 of the personal massager 100, as described with respect to FIGS. 45 to 46. The circular opening 409 at the back end of the tubular wall 405 (shown in FIGS. 43 and 44) may be stretched radially outward so as to fit over the front circular opening 711 (shown in FIGS. 59 to 61) at the front end of the housing 700, as shown in FIGS. 79 and 80. The internal flange 410 formed at or near the circular opening 409 may be received into the groove 706 defined by the first annular wall 704 and the external flange 705 at the front end of the housing 700, thereby detachably coupling the massage head 400 to the housing 700. The ridge (or ridges) 402 formed around the outer surface of the massage head may further secure the internal flange 410 within the groove 706.

Those skilled in the art will appreciate that the embodiments described herein are illustrative and not restrictive, and that modifications may occur depending upon design requirements without departing from the scope of the invention, as recited in the claims.

What is claimed is:

1. An apparatus comprising:
- a housing having a front end and a back end;
- a drive mechanism housed at least partially within said housing, said drive mechanism comprising:
  - a crank configured to move in a circular path;
  - means for creating a circular motion in said crank;
  - a rocker arm having a first end and a second end, said rocker arm being rotatably coupled at a first location on said rocker arm to said housing; and
  - an armature having a first end and a second end, said armature being rotatably coupled at a first location on said armature to said crank, and said armature being rotatably coupled at a second location on said armature to a second location on said rocker arm; and
- a massage head;
- wherein said armature and said massage head are configured to be directly coupled to one another.

2. The apparatus of claim 1 wherein said armature is rotatably coupled at a third location on said armature to a third location on said rocker arm.

3. The apparatus of claim 1 wherein said means for creating a circular motion in said crank comprises:
- a motor mounted within said housing; and
- a gear drive coupled to said motor and to said crank.

4. The apparatus of claim 3 wherein said gear drive comprises:
- a first gear coupled to a motor shaft extending from said motor; and
- a second gear coupled to an axle that is mounted within said housing;
- wherein said first gear and said second gear are mounted within said housing in such a manner that said first gear meshes with said second gear.

5. The apparatus of claim 4 wherein:
- said first gear comprises a worm; and
- said second gear comprises a worm gear.

6. The apparatus of claim 5 wherein said motor comprises a standard DC motor.

7. The apparatus of claim 4 wherein:
- said first gear comprises a bevel pinion gear; and
- said second gear comprises a bevel gear.

8. The apparatus of claim 7 wherein said motor comprises a gear motor.

9. The apparatus of claim 4 wherein said crank is coupled to said second gear.

10. The apparatus of claim 2 wherein said armature comprises:
- an armature body having a first end and a second end;
- a first arm having a first end and a second end, said first end of said first arm being coupled to said second end of said armature body; and
- a second arm having a first end and a second end, said first end of said second arm being coupled to said second end of said armature body.

11. The apparatus of claim 10 wherein said armature body and said massage head are configured to be directly coupled to one another.

12. The apparatus of claim 10 wherein said armature body comprises:
- a concave top surface;
- first and second convex side surfaces;
- a flat bottom surface;
- a rounded tip; and
- a flat back surface;
- wherein a first concave groove is formed in said first convex side surface, and a second concave groove is formed in said second convex side surface.

13. The apparatus of claim 12 wherein said massage head comprises a massage head body having a cavity formed therein, said cavity being configured to tightly house said armature body.

14. The apparatus of claim 10 wherein a first hole is formed in said first arm of said armature near its second end, said first hole being configured to receive said crank.

15. The apparatus of claim 10 wherein said rocker arm comprises:
- a cylindrical base having a first end and a second end;
- a first arm having a first end and a second end, said first end of said first arm of said rocker arm being orthogonally coupled to said first end of said cylindrical base, and said second end of said first arm of said rocker arm having a first projection coupled thereto; and
- a second arm having a first end and a second end, said first end of said second arm of said rocker arm being orthogonally coupled to said second end of said cylindrical base, and said second end of said second arm of said rocker arm having a second projection coupled thereto.

16. The apparatus of claim 15 wherein said rocker arm is rotatably coupled to said housing by a rocker cap.

17. The apparatus of claim 16 wherein said cylindrical base of said rocker arm is positioned between a semi-cylindrical groove formed in a rocker arm support extending forward from said front end of said housing and a semi-cylindrical groove formed in said rocker cap, and said rocker cap is coupled to said rocker arm support.

18. The apparatus of claim 15 wherein a second hole is formed in said first arm of said armature between its first end and said first hole, said second hole of said first arm being configured to receive said first projection of said rocker arm.

19. The apparatus of claim 18 wherein a third hole is formed in said second arm of said armature near its second end, said third hole of said second arm being coaxial with said second hole of said first arm and configured to receive said second projection of said rocker arm.

20. The apparatus of claim 1 wherein said first end of said armature extends through an opening formed in said front end of said housing, and said second end of said armature is supported within said housing.

21. The apparatus of claim 1 wherein said massage head comprises a massage head body having a front end and a back end, said massage head body and said armature being configured to be directly coupled to one another.

22. The apparatus of claim 21 wherein said massage head further comprises a tubular wall extending backward from said back end of said massage head body, said tubular wall and said housing being configured to be coupled to one another.

23. The apparatus of claim 22 wherein at least one corrugation is formed in said tubular wall of said massage head.

24. The apparatus of claim 22 wherein an internal flange is formed near said back end of said tubular wall of said massage head, said internal flange being configured to be received into an external groove formed near said front end of said housing.

25. The apparatus of claim 22 wherein at least one ridge is formed around the outer surface of said tubular wall near said back end of said tubular wall.

26. The apparatus of claim 1 further comprising a three-way rocker switch configured to control electrical communication between a power supply and said motor, said three-way rocker switch comprising:

a first terminal;

a second terminal; and a third terminal.

27. The apparatus of claim 26 wherein:

said first terminal of said three-way rocker switch is electrically coupled to a first terminal of said motor;

said second terminal of said three-way rocker switch is electrically coupled to a first terminal of said power supply;

said first terminal of said three-way rocker switch is electrically coupled to said third terminal of said three-way rocker switch through a diode; and a second terminal of said motor is coupled to a second terminal of said power supply.

28. The apparatus of claim 1 wherein:

said circular path of said crank defines a first plane; and said first end of said armature is configured to move in a closed plane path when said crank moves in said circular path, said closed plane path defining a second plane;

wherein said first plane is parallel to said second plane.

29. The apparatus of claim 28 wherein said massage head comprises:

a massage head body having a front end and a back end; and a tubular wall having a front end and a back end, said tubular wall extending backward from said back end of said massage head body, said tubular wall and said housing being configured to be coupled to one another;

and wherein said tubular wall is configured to deform when said crank moves in said circular path so as to allow said massage head body to follow said closed plane path of said first end of said armature.

30. The apparatus of claim 1 wherein said massage head is formed of silicone rubber.

31. The apparatus of claim 21 wherein said massage head body has an outer surface that simulates the shape of a human tongue.

32. The apparatus of claim 1 wherein said massage head has an outer surface that is at least partially textured to simulate the papillae on a human tongue.

33. The apparatus of claim 21 wherein said massage head body has a top surface having a shallow groove formed lengthwise along its centerline to simulate the median sulcus on a human tongue.

34. An apparatus comprising:

a housing having a front end and a back end;

a drive mechanism housed at least partially within said housing, said drive mechanism comprising:

a crank configured to move in a circular path;

means for creating a circular motion in said crank;

a rocker arm having a first end and a second end, said rocker arm being rotatably coupled at a first location on said rocker arm to said housing; and an armature having a first end and a second end, said armature being rotatably coupled at a first location on said armature to said crank, said first location on said armature being at or near said second end of said armature, and said armature being rotatably coupled at a second location on said armature to a second location on said rocker arm, said second location on said armature being an intermediate location between said first end and said second end of said armature; and a massage head;

wherein said armature and said massage head are configured to be coupled to one another.

* * * * *